United States Patent
Spargias

(10) Patent No.: US 12,138,160 B2
(45) Date of Patent: *Nov. 12, 2024

(54) TRANSCATHETER PROSTHETIC HEART VALVE AND DELIVERY SYSTEM

(71) Applicant: Edwards Lifesciences Corporation, Irvine, CA (US)

(72) Inventor: Konstantinos Spargias, Athens (GR)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 161 days.

This patent is subject to a terminal disclaimer.

(21) Appl. No.: 18/095,979

(22) Filed: Jan. 11, 2023

(65) Prior Publication Data
US 2023/0157818 A1 May 25, 2023

Related U.S. Application Data

(63) Continuation of application No. 16/740,916, filed on Jan. 13, 2020, now Pat. No. 11,559,395, which is a
(Continued)

(30) Foreign Application Priority Data

Nov. 26, 2014 (GR) .............................. 20140100595

(51) Int. Cl.
*A61F 2/24* (2006.01)

(52) U.S. Cl.
CPC .......... *A61F 2/2418* (2013.01); *A61F 2/2436* (2013.01); *A61F 2210/0014* (2013.01);
(Continued)

(58) Field of Classification Search
CPC ........ A61F 2/24; A61F 2/2427; A61F 2/2418; A61F 2/2436; A61F 2/2412; A61F 2/2466; A61F 2017/0078
See application file for complete search history.

(56) References Cited

U.S. PATENT DOCUMENTS

| 3,409,013 A | 11/1968 | Berry |
| 3,472,230 A | 10/1969 | Fogarty |

(Continued)

FOREIGN PATENT DOCUMENTS

| CA | 2304325 A1 | 10/2000 |
| DE | 2246526 A1 | 3/1973 |

(Continued)

OTHER PUBLICATIONS

Al Zaibag et al., "Percutaneous Balloon Valvotomy in Tricuspid Stenosis", British Heart Journal, vol. 57, No. 1, Jan. 1987.
(Continued)

*Primary Examiner* — Vi X Nguyen
(74) *Attorney, Agent, or Firm* — Thomas C. Richardson

(57) ABSTRACT

A method of implanting a prosthetic heart valve includes advancing a delivery catheter toward a native heart valve, wherein the delivery catheter has a distal capsule containing a prosthetic valve in a compressed state. The prosthetic valve includes a self-expandable interior stent and a self-expandable exterior wire mesh surrounding the interior stent. The exterior wire mesh preferably has a lower radial strength than the interior stent for conforming to a surrounding shape of the native valve. The prosthetic valve is expelled from the distal capsule and allowed to expand within the native valve. Capturing elements extending from a ventricular end of the interior stent trap native leaflets between the capturing elements and an outer surface of the wire mesh.

18 Claims, 16 Drawing Sheets

Related U.S. Application Data continuation of application No. 15/526,810, filed as application No. PCT/EP2015/077856 on Nov. 26, 2015, now Pat. No. 10,531,951.

(52) U.S. Cl.
CPC .............. *A61F 2220/0008* (2013.01); *A61F 2220/0016* (2013.01); *A61F 2250/0063* (2013.01)

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,739,402 A | 6/1973 | Cooley et al. |
| 3,755,823 A | 9/1973 | Hancock |
| 4,035,849 A | 7/1977 | Angell et al. |
| 4,056,854 A | 11/1977 | Boretos et al. |
| 4,079,468 A | 3/1978 | Liotta et al. |
| 4,106,129 A | 8/1978 | Carpentier et al. |
| 4,204,283 A | 5/1980 | Bellhouse et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,340,977 A | 7/1982 | Brownlee et al. |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,477,930 A | 10/1984 | Totten et al. |
| 4,490,859 A | 1/1985 | Black et al. |
| 4,535,483 A | 8/1985 | Klawitter et al. |
| 4,553,545 A | 11/1985 | Maass et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,865,600 A | 9/1989 | Carpentier et al. |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,108,370 A | 4/1992 | Walinsky |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,232,446 A | 8/1993 | Arney |
| 5,266,073 A | 11/1993 | Wall |
| 5,282,847 A | 2/1994 | Trescony et al. |
| 5,295,958 A | 3/1994 | Shturman |
| 5,326,371 A | 7/1994 | Love et al. |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,522 A | 5/1995 | Trott |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,591,185 A | 1/1997 | Kilmer et al. |
| 5,599,305 A | 2/1997 | Hermann et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,697,382 A | 12/1997 | Love et al. |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,906,619 A | 5/1999 | Olson et al. |
| 5,925,063 A | 7/1999 | Khosravi |
| 5,957,949 A | 9/1999 | Leonhardt et al. |
| 5,968,068 A | 10/1999 | Dehdashtian et al. |
| 6,027,525 A | 2/2000 | Suh et al. |
| 6,042,607 A | 3/2000 | Williamson, IV et al. |
| 6,086,612 A | 7/2000 | Jansen |
| 6,113,631 A | 9/2000 | Jansen |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,040 B1 | 6/2001 | Inderbitzen et al. |
| 6,245,100 B1 * | 6/2001 | Davila .................... A61F 2/91 606/198 |
| 6,245,102 B1 | 6/2001 | Jayaraman |
| 6,251,093 B1 | 6/2001 | Valley et al. |
| 6,287,339 B1 | 9/2001 | Vazquez et al. |
| 6,299,637 B1 | 10/2001 | Shaolian et al. |
| 6,302,906 B1 | 10/2001 | Goecoechea et al. |
| 6,306,141 B1 | 10/2001 | Jervis |
| 6,312,465 B1 | 11/2001 | Griffin et al. |
| 6,350,277 B1 | 2/2002 | Kocur |
| 6,358,277 B1 | 3/2002 | Duran |
| 6,379,372 B1 | 4/2002 | Dehdashtian et al. |
| 6,425,916 B1 | 7/2002 | Garrison et al. |
| 6,440,164 B1 | 8/2002 | Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,800 B1 | 3/2003 | McGuckin, Jr. et al. |

(56) References Cited

U.S. PATENT DOCUMENTS

| | | |
|---|---|---|
| 6,527,979 B2 | 3/2003 | Constantz |
| 6,540,782 B1 | 4/2003 | Snyders |
| 6,569,196 B1 | 5/2003 | Vesely |
| 6,575,959 B1 | 6/2003 | Sarge et al. |
| 6,582,462 B1 | 6/2003 | Andersen et al. |
| 6,605,112 B1 | 8/2003 | Moll et al. |
| 6,610,088 B1 | 8/2003 | Gabbay |
| 6,629,534 B1 | 10/2003 | St. Goar et al. |
| 6,676,698 B2 | 1/2004 | McGuckin, Jr. et al. |
| 6,695,878 B2 | 2/2004 | McGuckin, Jr. et al. |
| 6,712,836 B1 | 3/2004 | Berg et al. |
| 6,716,207 B2 | 4/2004 | Farnholtz |
| 6,729,356 B1 | 5/2004 | Baker et al. |
| 6,730,118 B2 | 5/2004 | Spenser et al. |
| 6,733,525 B2 | 5/2004 | Yang et al. |
| 6,746,422 B1 | 6/2004 | Noriega et al. |
| 6,749,560 B1 | 6/2004 | Konstorum et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,830,584 B1 | 12/2004 | Seguin |
| 6,875,231 B2 | 4/2005 | Anduiza et al. |
| 6,893,460 B2 | 5/2005 | Spenser et al. |
| 6,908,481 B2 | 6/2005 | Cribier |
| 6,974,476 B2 | 12/2005 | McGuckin, Jr. et al. |
| 7,018,406 B2 | 3/2006 | Seguin et al. |
| 7,186,265 B2 | 3/2007 | Sharkawy et al. |
| 7,192,440 B2 | 3/2007 | Andreas et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,381,210 B2 | 6/2008 | Zarbatany et al. |
| 7,381,219 B2 | 6/2008 | Salahieh et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,530,253 B2 | 5/2009 | Spenser et al. |
| 7,553,324 B2 | 6/2009 | Andreas et al. |
| 7,579,381 B2 | 8/2009 | Dove |
| 7,585,321 B2 | 9/2009 | Cribier |
| 7,618,446 B2 | 11/2009 | Andersen et al. |
| 7,621,948 B2 | 11/2009 | Herrmann et al. |
| 7,704,222 B2 | 4/2010 | Wilk et al. |
| 7,736,327 B2 | 6/2010 | Wilk et al. |
| 7,748,389 B2 | 7/2010 | Salahieh et al. |
| 7,753,949 B2 | 7/2010 | Lamphere et al. |
| 7,806,919 B2 | 10/2010 | Bloom et al. |
| 7,824,443 B2 | 11/2010 | Salahieh et al. |
| 7,837,727 B2 | 11/2010 | Goetz et al. |
| 7,892,281 B2 | 2/2011 | Seguin et al. |
| 7,914,569 B2 | 3/2011 | Nguyen et al. |
| 7,914,575 B2 | 3/2011 | Guyenot et al. |
| 7,959,672 B2 | 6/2011 | Salahieh et al. |
| 7,972,378 B2 | 7/2011 | Tabor et al. |
| 7,981,151 B2 | 7/2011 | Rowe |
| 7,993,392 B2 | 8/2011 | Righini et al. |
| 7,993,394 B2 | 8/2011 | Hariton et al. |
| 8,007,992 B2 | 8/2011 | Tian et al. |
| 8,016,877 B2 | 9/2011 | Seguin et al. |
| 8,029,556 B2 | 10/2011 | Rowe |
| 8,052,750 B2 | 11/2011 | Tuval et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,092,520 B2 | 1/2012 | Quadri |
| 8,092,521 B2 | 1/2012 | Figulla et al. |
| 8,109,996 B2 | 2/2012 | Stacchino et al. |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,167,932 B2 | 5/2012 | Bourang |
| 8,167,934 B2 | 5/2012 | Styrc et al. |
| 8,182,530 B2 | 5/2012 | Huber |
| 8,206,437 B2 | 6/2012 | Bonhoeffer et al. |
| 8,216,174 B2 | 7/2012 | Wilk et al. |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,236,045 B2 | 8/2012 | Benichou et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,313,525 B2 | 11/2012 | Tuval et al. |
| 8,317,858 B2 | 11/2012 | Straubinger et al. |
| 8,323,335 B2 | 12/2012 | Rowe et al. |
| 8,337,541 B2 | 12/2012 | Quadri et al. |
| 8,353,953 B2 | 1/2013 | Giannetti et al. |
| 8,398,704 B2 | 3/2013 | Straubinger et al. |
| 8,403,983 B2 | 3/2013 | Quadri et al. |
| 8,414,644 B2 | 4/2013 | Quadri et al. |
| 8,414,645 B2 | 4/2013 | Dwork et al. |
| 8,416,643 B2 | 4/2013 | Magee |
| 8,444,689 B2 | 5/2013 | Zhang |
| 8,449,599 B2 | 5/2013 | Chau et al. |
| 8,454,685 B2 | 6/2013 | Hariton et al. |
| 8,460,368 B2 | 6/2013 | Taylor et al. |
| 8,460,370 B2 | 6/2013 | Zakay |
| 8,470,023 B2 | 6/2013 | Eidenschink et al. |
| 8,470,028 B2 | 6/2013 | Thornton et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,491,650 B2 | 7/2013 | Wiemeyer et al. |
| 8,500,733 B2 | 8/2013 | Watson |
| 8,500,798 B2 | 8/2013 | Rowe et al. |
| 8,511,244 B2 | 8/2013 | Holecek et al. |
| 8,512,401 B2 | 8/2013 | Murray, III et al. |
| 8,518,096 B2 | 8/2013 | Nelson |
| 8,518,106 B2 | 8/2013 | Duffy et al. |
| 8,562,663 B2 | 10/2013 | Mearns et al. |
| 8,579,963 B2 | 11/2013 | Tabor |
| 8,579,964 B2 | 11/2013 | Lane et al. |
| 8,591,570 B2 | 11/2013 | Revuelta et al. |
| 8,617,236 B2 | 12/2013 | Paul et al. |
| 8,640,521 B2 | 2/2014 | Righini et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,202 B2 | 2/2014 | Alon et al. |
| 8,652,203 B2 | 2/2014 | Quadri et al. |
| 8,668,733 B2 | 3/2014 | Haug et al. |
| 8,679,174 B2 | 3/2014 | Ottma et al. |
| 8,679,404 B2 | 3/2014 | Liburd et al. |
| 8,685,086 B2 | 4/2014 | Navia et al. |
| 8,721,708 B2 | 5/2014 | Seguin et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,758,432 B2 | 6/2014 | Solem |
| 8,764,818 B2 | 7/2014 | Gregg |
| 8,771,344 B2 | 7/2014 | Tran et al. |
| 8,778,020 B2 | 7/2014 | Gregg et al. |
| 8,784,337 B2 | 7/2014 | Voeller et al. |
| 8,784,478 B2 | 7/2014 | Tuval et al. |
| 8,784,481 B2 | 7/2014 | Alkhatib et al. |
| 8,790,387 B2 | 7/2014 | Nguyen et al. |
| 8,795,357 B2 | 8/2014 | Yohanan et al. |
| 8,808,356 B2 | 8/2014 | Braido et al. |

(56) References Cited

U.S. PATENT DOCUMENTS

| | | |
|---|---|---|
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,858,620 B2 | 10/2014 | Salahieh et al. |
| 8,870,948 B1 | 10/2014 | Erzberger et al. |
| 8,870,950 B2 | 10/2014 | Hacohen |
| 8,876,893 B2 | 11/2014 | Dwork et al. |
| 8,911,455 B2 | 12/2014 | Quadri et al. |
| 8,926,693 B2 | 1/2015 | Duffy et al. |
| 8,926,694 B2 | 1/2015 | Costello |
| 8,939,960 B2 | 1/2015 | Rosenman et al. |
| 8,945,209 B2 | 2/2015 | Bonyuet et al. |
| 8,961,593 B2 | 2/2015 | Bonhoeffer et al. |
| 8,961,595 B2 | 2/2015 | Alkhatib |
| 8,974,524 B2 | 3/2015 | Yeung et al. |
| 8,979,922 B2 | 3/2015 | Jayasinghe et al. |
| 8,986,375 B2 | 3/2015 | Garde et al. |
| 8,998,980 B2 | 4/2015 | Shipley et al. |
| 9,005,273 B2 | 4/2015 | Salahieh et al. |
| 9,011,521 B2 | 4/2015 | Haug et al. |
| 9,011,523 B2 | 4/2015 | Seguin |
| 9,011,524 B2 | 4/2015 | Eberhardt |
| 9,028,545 B2 | 5/2015 | Taylor |
| 9,034,032 B2 | 5/2015 | McLean et al. |
| 9,055,937 B2 | 6/2015 | Rowe et al. |
| 9,066,801 B2 | 6/2015 | Kovalsky et al. |
| 9,078,749 B2 | 7/2015 | Lutter et al. |
| 9,078,751 B2 | 7/2015 | Naor |
| 9,125,738 B2 | 9/2015 | Figulla et al. |
| 9,173,737 B2 | 11/2015 | Hill et al. |
| 9,180,004 B2 | 11/2015 | Alkhatib |
| 9,186,249 B2 | 11/2015 | Rolando et al. |
| 9,277,990 B2 | 3/2016 | Klima et al. |
| 9,277,993 B2 | 3/2016 | Gamarra et al. |
| 9,289,291 B2 | 3/2016 | Gorman, III et al. |
| 9,295,551 B2 | 3/2016 | Straubinger et al. |
| 9,445,897 B2 | 9/2016 | Bishop et al. |
| 9,456,877 B2 | 10/2016 | Weitzner et al. |
| 9,681,968 B2 | 6/2017 | Goetz et al. |
| 9,687,345 B2 | 6/2017 | Rabito et al. |
| 9,700,329 B2 | 7/2017 | Metzger et al. |
| 9,700,411 B2 | 7/2017 | Klima et al. |
| 9,724,083 B2 | 8/2017 | Quadri et al. |
| 9,730,790 B2 | 8/2017 | Quadri et al. |
| 9,730,791 B2 | 8/2017 | Ratz et al. |
| 9,795,479 B2 | 10/2017 | Lim et al. |
| 9,833,313 B2 | 12/2017 | Board et al. |
| 9,861,473 B2 | 1/2018 | Lafontaine |
| 9,861,476 B2 | 1/2018 | Salahieh et al. |
| 9,861,477 B2 | 1/2018 | Backus et al. |
| 9,867,698 B2 | 1/2018 | Kovalsky et al. |
| 9,877,830 B2 | 1/2018 | Lim et al. |
| 9,889,029 B2 | 2/2018 | Li et al. |
| 9,895,225 B2 | 2/2018 | Rolando et al. |
| 9,925,045 B2 | 3/2018 | Creaven et al. |
| 10,004,599 B2 | 6/2018 | Rabito et al. |
| 10,117,744 B2 | 11/2018 | Ratz et al. |
| 10,179,044 B2 | 1/2019 | Ratz et al. |
| 10,219,897 B2 | 3/2019 | Essinger et al. |
| 10,350,065 B2 | 7/2019 | Quadri |
| 10,350,066 B2 | 7/2019 | Cooper et al. |
| 10,376,363 B2 | 8/2019 | Quadri et al. |
| 10,531,951 B2 * | 1/2020 | Spargias ............ A61F 2/2418 |
| 10,555,809 B2 | 2/2020 | Hastings et al. |
| 10,575,951 B2 | 3/2020 | Johnson et al. |
| 10,583,000 B2 | 3/2020 | Ratz et al. |
| 10,639,146 B2 | 5/2020 | Quadri et al. |
| 10,695,177 B2 | 6/2020 | Hariton et al. |
| 10,758,344 B2 | 9/2020 | Hariton et al. |
| 11,406,499 B2 | 8/2022 | Zhang et al. |
| 11,452,598 B2 | 9/2022 | Essinger et al. |
| 11,559,395 B2 * | 1/2023 | Spargias ............ A61F 2/2436 |
| 11,672,658 B2 | 6/2023 | Hariton et al. |
| 11,701,225 B2 | 7/2023 | Hammer et al. |
| 11,903,829 B1 | 2/2024 | Ma et al. |
| 2001/0021872 A1 | 9/2001 | Bailey et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2002/0173842 A1 | 11/2002 | Buchanan |
| 2003/0050694 A1 | 3/2003 | Yang et al. |
| 2003/0100939 A1 | 5/2003 | Yodfat et al. |
| 2003/0105517 A1 | 6/2003 | White et al. |
| 2003/0120333 A1 | 6/2003 | Ouriel et al. |
| 2003/0130729 A1 | 7/2003 | Paniagua et al. |
| 2003/0158597 A1 | 8/2003 | Quiachon et al. |
| 2003/0176914 A1 | 9/2003 | Rabkin et al. |
| 2003/0199971 A1 | 10/2003 | Tower et al. |
| 2003/0212454 A1 | 11/2003 | Scott et al. |
| 2003/0220683 A1 | 11/2003 | Minasian et al. |
| 2004/0039436 A1 | 2/2004 | Spenser et al. |
| 2004/0092858 A1 | 5/2004 | Wilson et al. |
| 2004/0117009 A1 | 6/2004 | Cali et al. |
| 2004/0133263 A1 | 7/2004 | Dusbabek et al. |
| 2004/0133273 A1 | 7/2004 | Cox |
| 2004/0186563 A1 | 9/2004 | Lobbi |
| 2004/0186565 A1 | 9/2004 | Schreck |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2004/0260389 A1 | 12/2004 | Case et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137691 A1 | 6/2005 | Salahieh et al. |
| 2005/0137698 A1 | 6/2005 | Salahieh et al. |
| 2005/0159811 A1 | 7/2005 | Lane |
| 2005/0182486 A1 | 8/2005 | Gabbay |
| 2005/0203614 A1 | 9/2005 | Forster et al. |
| 2005/0203617 A1 | 9/2005 | Forster et al. |
| 2005/0216079 A1 | 9/2005 | MaCoviak |
| 2005/0234546 A1 | 10/2005 | Nugent et al. |
| 2005/0288766 A1 | 12/2005 | Plain et al. |
| 2006/0020327 A1 | 1/2006 | Lashinski et al. |
| 2006/0025857 A1 | 2/2006 | Bergheim et al. |
| 2006/0058872 A1 | 3/2006 | Salahieh et al. |
| 2006/0095115 A1 | 5/2006 | Bladillah et al. |
| 2006/0142837 A1 | 6/2006 | Haverkost et al. |
| 2006/0149350 A1 | 7/2006 | Patel et al. |
| 2006/0161249 A1 | 7/2006 | Realyvasquez et al. |
| 2006/0173537 A1 | 8/2006 | Yang et al. |
| 2006/0195134 A1 | 8/2006 | Crittenden |
| 2006/0195183 A1 | 8/2006 | Navia et al. |
| 2006/0212110 A1 | 9/2006 | Osborne et al. |
| 2006/0229719 A1 | 10/2006 | Marquez et al. |
| 2006/0241745 A1 | 10/2006 | Solem |
| 2006/0259135 A1 | 11/2006 | Navia et al. |
| 2006/0259137 A1 | 11/2006 | Artof et al. |
| 2006/0276874 A1 | 12/2006 | Wilson et al. |
| 2006/0293745 A1 | 12/2006 | Carpentier et al. |
| 2007/0005131 A1 | 1/2007 | Taylor |
| 2007/0010877 A1 | 1/2007 | Salahieh et al. |
| 2007/0027534 A1 | 2/2007 | Bergheim et al. |
| 2007/0043435 A1 | 2/2007 | Seguin et al. |
| 2007/0050021 A1 | 3/2007 | Johnson |
| 2007/0066863 A1 | 3/2007 | Rafiee et al. |
| 2007/0088431 A1 | 4/2007 | Bourang et al. |
| 2007/0100432 A1 | 5/2007 | Case et al. |
| 2007/0100439 A1 | 5/2007 | Cangialosi et al. |
| 2007/0112422 A1 | 5/2007 | Dehdashtian |
| 2007/0129794 A1 | 6/2007 | Realyvasquez |
| 2007/0142906 A1 | 6/2007 | Figulla et al. |
| 2007/0156224 A1 | 7/2007 | Cioanta et al. |
| 2007/0203503 A1 | 8/2007 | Salahieh et al. |
| 2007/0203575 A1 | 8/2007 | Forster et al. |
| 2007/0213813 A1 | 9/2007 | Von Segesser et al. |
| 2007/0255394 A1 | 11/2007 | Ryan |

(56) References Cited

U.S. PATENT DOCUMENTS

| | | |
|---|---|---|
| 2007/0270943 A1 | 11/2007 | Solem et al. |
| 2008/0021546 A1 | 1/2008 | Patz et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0097581 A1 | 4/2008 | Shanley |
| 2008/0114442 A1 | 5/2008 | Mitchell et al. |
| 2008/0125853 A1 | 5/2008 | Bailey et al. |
| 2008/0147179 A1 | 6/2008 | Cai et al. |
| 2008/0147183 A1 | 6/2008 | Styrc |
| 2008/0154355 A1 | 6/2008 | Benichou et al. |
| 2008/0177381 A1 | 7/2008 | Navia et al. |
| 2008/0183273 A1 | 7/2008 | Mesana et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0228254 A1 | 9/2008 | Ryan |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2009/0005863 A1 | 1/2009 | Goetz et al. |
| 2009/0054968 A1 | 2/2009 | Bonhoeffer et al. |
| 2009/0054974 A1 | 2/2009 | McGuckin, Jr. et al. |
| 2009/0076598 A1 | 3/2009 | Salahieh et al. |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0182413 A1 | 7/2009 | Burkart et al. |
| 2009/0188964 A1 | 7/2009 | Orlov |
| 2009/0216310 A1 | 8/2009 | Straubinger et al. |
| 2009/0216313 A1 | 8/2009 | Straubinger et al. |
| 2009/0216322 A1 | 8/2009 | Le et al. |
| 2009/0222076 A1 | 9/2009 | Figulla et al. |
| 2009/0234443 A1 | 9/2009 | Ottma et al. |
| 2009/0240320 A1 | 9/2009 | Tuval et al. |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0292350 A1 | 11/2009 | Eberhardt et al. |
| 2009/0306768 A1 | 12/2009 | Quadri |
| 2009/0319037 A1 | 12/2009 | Rowe et al. |
| 2010/0016958 A1 | 1/2010 | St. Goar et al. |
| 2010/0049313 A1 | 2/2010 | Alon et al. |
| 2010/0069852 A1 | 3/2010 | Kelley |
| 2010/0114305 A1 | 5/2010 | Kang et al. |
| 2010/0131054 A1 | 5/2010 | Tuval et al. |
| 2010/0137979 A1 | 6/2010 | Tuval et al. |
| 2010/0174362 A1 | 7/2010 | Straubinger et al. |
| 2010/0191326 A1 | 7/2010 | Alkhatib |
| 2010/0204781 A1 | 8/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0262231 A1 | 10/2010 | Tuval et al. |
| 2010/0305685 A1 | 12/2010 | Millwee et al. |
| 2011/0015616 A1 | 1/2011 | Straubinger et al. |
| 2011/0015729 A1 | 1/2011 | Jimenez et al. |
| 2011/0137397 A1 | 6/2011 | Chau et al. |
| 2011/0208290 A1 | 8/2011 | Straubinger et al. |
| 2011/0208297 A1 | 8/2011 | Tuval et al. |
| 2011/0208298 A1 | 8/2011 | Tuval et al. |
| 2011/0224785 A1* | 9/2011 | Hacohen ............... A61F 2/2457 623/2.18 |
| 2011/0238159 A1 | 9/2011 | Guyenot et al. |
| 2011/0264196 A1 | 10/2011 | Savage et al. |
| 2011/0264198 A1 | 10/2011 | Murray, III et al. |
| 2011/0288634 A1 | 11/2011 | Tuval et al. |
| 2011/0313515 A1 | 12/2011 | Quadri et al. |
| 2011/0319989 A1 | 12/2011 | Lane et al. |
| 2012/0022639 A1 | 1/2012 | Hacohen et al. |
| 2012/0035722 A1 | 2/2012 | Tuval |
| 2012/0041550 A1 | 2/2012 | Salahieh et al. |
| 2012/0046741 A1 | 2/2012 | Tuval et al. |
| 2012/0046742 A1 | 2/2012 | Tuval et al. |
| 2012/0078360 A1 | 3/2012 | Rafiee |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0185039 A1 | 7/2012 | Tuval et al. |
| 2012/0197386 A1 | 8/2012 | Von Segesser et al. |
| 2012/0209374 A1 | 8/2012 | Bonhoeffer et al. |
| 2012/0215303 A1 | 8/2012 | Quadri et al. |
| 2012/0271398 A1 | 10/2012 | Essinger et al. |
| 2012/0283823 A1 | 11/2012 | Bonhoeffer et al. |
| 2012/0290062 A1 | 11/2012 | McNamara et al. |
| 2012/0296418 A1 | 11/2012 | Bonyuet et al. |
| 2012/0310328 A1 | 12/2012 | Olson et al. |
| 2012/0310336 A1 | 12/2012 | Figulla et al. |
| 2013/0006294 A1 | 1/2013 | Kashkarov et al. |
| 2013/0035759 A1 | 2/2013 | Gross et al. |
| 2013/0073035 A1 | 3/2013 | Tuval et al. |
| 2013/0079869 A1 | 3/2013 | Straubinger et al. |
| 2013/0190861 A1 | 7/2013 | Chau et al. |
| 2013/0190862 A1 | 7/2013 | Pintor et al. |
| 2013/0197622 A1 | 8/2013 | Mitra et al. |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0310928 A1* | 11/2013 | Morriss ............... A61F 2/2409 623/2.18 |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0018912 A1 | 1/2014 | Delaloye et al. |
| 2014/0025163 A1 | 1/2014 | Padala et al. |
| 2014/0039611 A1 | 2/2014 | Lane et al. |
| 2014/0052237 A1 | 2/2014 | Lane et al. |
| 2014/0100651 A1 | 4/2014 | Kheradvar et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214157 A1 | 7/2014 | Bortlein et al. |
| 2014/0222139 A1 | 8/2014 | Nguyen et al. |
| 2014/0222142 A1 | 8/2014 | Kovalsky et al. |
| 2014/0222144 A1 | 8/2014 | Eberhardt et al. |
| 2014/0243966 A1 | 8/2014 | Garde et al. |
| 2014/0257467 A1 | 9/2014 | Lane et al. |
| 2014/0277390 A1 | 9/2014 | Ratz et al. |
| 2014/0277412 A1 | 9/2014 | Bortlein et al. |
| 2014/0277422 A1 | 9/2014 | Ratz et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0350666 A1 | 11/2014 | Righini |
| 2014/0350668 A1 | 11/2014 | Delaloye et al. |

(56) References Cited

U.S. PATENT DOCUMENTS

| | | |
|---|---|---|
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371847 A1 | 12/2014 | Madrid et al. |
| 2014/0371848 A1 | 12/2014 | Murray, III et al. |
| 2015/0005863 A1 | 1/2015 | Para |
| 2015/0018944 A1 | 1/2015 | O'Connell et al. |
| 2015/0039083 A1 | 2/2015 | Rafiee |
| 2015/0142103 A1 | 5/2015 | Vidlund |
| 2015/0148731 A1 | 5/2015 | McNamara et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0272737 A1 | 10/2015 | Dale et al. |
| 2015/0297346 A1 | 10/2015 | Duffy et al. |
| 2015/0305860 A1* | 10/2015 | Wang .................. A61F 2/2409 623/2.38 |
| 2015/0335429 A1 | 11/2015 | Morriss et al. |
| 2015/0351903 A1 | 12/2015 | Morriss et al. |
| 2015/0359629 A1 | 12/2015 | Ganesan et al. |
| 2016/0000591 A1 | 1/2016 | Lei et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113768 A1 | 4/2016 | Ganesan et al. |
| 2016/0143732 A1 | 5/2016 | Glimsdale |
| 2016/0158010 A1 | 6/2016 | Lim et al. |
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0213473 A1 | 7/2016 | Hacohen et al. |
| 2016/0235529 A1 | 8/2016 | Ma et al. |
| 2016/0279386 A1 | 9/2016 | Dale et al. |
| 2016/0310267 A1 | 10/2016 | Zeng et al. |
| 2017/0128209 A1 | 5/2017 | Morriss et al. |
| 2017/0216023 A1 | 8/2017 | Lane et al. |
| 2017/0216575 A1 | 8/2017 | Asleson et al. |
| 2017/0258614 A1 | 9/2017 | Griffin |
| 2017/0325954 A1 | 11/2017 | Perszyk |
| 2017/0348096 A1 | 12/2017 | Anderson |
| 2017/0367821 A1 | 12/2017 | Landon et al. |
| 2017/0367823 A1 | 12/2017 | Hariton et al. |
| 2018/0021129 A1 | 1/2018 | Peterson et al. |
| 2018/0055629 A1 | 3/2018 | Oba et al. |
| 2018/0055636 A1 | 3/2018 | Valencia et al. |
| 2018/0085218 A1 | 3/2018 | Eidenschink |
| 2018/0110534 A1 | 4/2018 | Gavala et al. |
| 2018/0116790 A1 | 5/2018 | Ratz et al. |
| 2019/0008639 A1 | 1/2019 | Landon et al. |
| 2019/0008640 A1 | 1/2019 | Cooper et al. |
| 2019/0262129 A1 | 8/2019 | Cooper et al. |
| 2020/0000579 A1 | 1/2020 | Manash et al. |
| 2020/0108225 A1 | 4/2020 | Jamal et al. |
| 2020/0345494 A1 | 11/2020 | Srinimukesh et al. |
| 2020/0352718 A1 | 11/2020 | Rowe et al. |
| 2021/0145576 A1 | 5/2021 | Becerra et al. |
| 2021/0378817 A1 | 12/2021 | Nia et al. |
| 2021/0386544 A1 | 12/2021 | Cooper et al. |
| 2022/0142777 A1 | 5/2022 | Scheinblum et al. |
| 2022/0287836 A1 | 9/2022 | Landon et al. |
| 2022/0346993 A1 | 11/2022 | Srinimukesh et al. |
| 2023/0000624 A1 | 1/2023 | Okabe et al. |
| 2023/0200980 A1 | 6/2023 | Peterson et al. |
| 2023/0218391 A1 | 7/2023 | Dass et al. |
| 2023/0380963 A1 | 11/2023 | Kaufman et al. |
| 2023/0390052 A1 | 12/2023 | Okafor et al. |
| 2023/0404753 A1 | 12/2023 | Luong et al. |
| 2024/0008978 A1 | 1/2024 | Nawalakhe et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10010074 A1 | 10/2001 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 102006052564 B3 | 12/2007 |
| EP | 0103546 A1 | 3/1984 |
| EP | 0144167 A2 | 6/1985 |
| EP | 0592410 A1 | 4/1994 |
| EP | 0597967 A1 | 5/1994 |
| EP | 0850607 A1 | 7/1998 |
| EP | 1057460 A1 | 12/2000 |
| EP | 1088529 A2 | 4/2001 |
| EP | 1171059 A1 | 1/2002 |
| EP | 1239901 A1 | 9/2002 |
| EP | 1255510 A1 | 11/2002 |
| EP | 1259194 A1 | 11/2002 |
| EP | 1369098 A1 | 12/2003 |
| EP | 1469797 A1 | 10/2004 |
| EP | 1472996 A1 | 11/2004 |
| EP | 1570809 A1 | 9/2005 |
| EP | 1653888 A2 | 5/2006 |
| EP | 1849440 A1 | 10/2007 |
| EP | 1935377 A1 | 6/2008 |
| EP | 2124826 A1 | 12/2009 |
| EP | 2168536 A1 | 3/2010 |
| EP | 2413842 A1 | 2/2012 |
| EP | 2446915 A1 | 5/2012 |
| EP | 2745805 A1 | 6/2014 |
| EP | 2749254 A1 | 7/2014 |
| EP | 2750630 A1 | 7/2014 |
| EP | 2777616 A1 | 9/2014 |
| EP | 2777617 A1 | 9/2014 |
| EP | 2918249 A2 | 9/2015 |
| EP | 2948103 A2 | 12/2015 |
| EP | 2967858 A2 | 1/2016 |
| EP | 3037064 A1 | 6/2016 |
| EP | 3046511 A2 | 7/2016 |
| EP | 3057541 A1 | 8/2016 |
| EP | 3075354 A2 | 10/2016 |
| EP | 3139864 A1 | 3/2017 |
| EP | 3142603 A1 | 3/2017 |
| EP | 3184083 A1 | 6/2017 |
| EP | 3294220 A1 | 3/2018 |
| EP | 3417813 A1 | 12/2018 |
| EP | 3570779 A1 | 11/2019 |
| FR | 2788217 A1 | 7/2000 |
| FR | 2815844 A1 | 5/2002 |
| GB | 1264471 A | 2/1972 |
| GB | 1315844 A | 5/1973 |
| GB | 2056023 A | 3/1981 |
| GB | 2398245 A | 8/2004 |
| SU | 1271508 A1 | 11/1986 |
| WO | 9116041 A1 | 10/1991 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9933414 A1 | 7/1999 |
| WO | 9940964 A1 | 8/1999 |
| WO | 9947075 A1 | 9/1999 |
| WO | 0047139 A1 | 8/2000 |
| WO | 03047468 A1 | 6/2003 |
| WO | 03092554 A1 | 11/2003 |
| WO | 2004030569 A2 | 4/2004 |
| WO | 2004100652 A2 | 11/2004 |
| WO | 2005011534 A1 | 2/2005 |
| WO | 2005034812 A1 | 4/2005 |
| WO | 2005087140 A1 | 9/2005 |
| WO | 2005102015 A2 | 11/2005 |
| WO | 2006014233 A2 | 2/2006 |
| WO | 2006034008 A2 | 3/2006 |

(56) References Cited

FOREIGN PATENT DOCUMENTS

| | | |
|---|---|---|
| WO | 2006085225 A1 | 8/2006 |
| WO | 2006100034 A1 | 9/2006 |
| WO | 2006108090 A2 | 10/2006 |
| WO | 2006111391 A1 | 10/2006 |
| WO | 2006138173 A2 | 12/2006 |
| WO | 2007025028 A1 | 3/2007 |
| WO | 2008005405 A2 | 1/2008 |
| WO | 2008035337 A2 | 3/2008 |
| WO | 2008125153 A1 | 10/2008 |
| WO | 2008147964 A1 | 12/2008 |
| WO | 2008150529 A1 | 12/2008 |
| WO | 2009024859 A2 | 2/2009 |
| WO | 2009026563 A2 | 2/2009 |
| WO | 2009042196 A2 | 4/2009 |
| WO | 2009091509 A1 | 7/2009 |
| WO | 2009094500 A1 | 7/2009 |
| WO | 2010005524 A2 | 1/2010 |
| WO | 2010008549 A1 | 1/2010 |
| WO | 2010121076 A2 | 10/2010 |
| WO | 2011002996 A2 | 1/2011 |
| WO | 2011081997 A1 | 7/2011 |
| WO | 2012008459 A1 | 1/2012 |
| WO | 2012032187 A1 | 3/2012 |
| WO | 2012095455 A2 | 7/2012 |
| WO | 2013005878 A1 | 1/2013 |
| WO | 2013028387 A2 | 2/2013 |
| WO | 2013106585 A1 | 7/2013 |
| WO | 2014009213 A1 | 1/2014 |
| WO | 2014018432 A2 | 1/2014 |
| WO | 2014079291 A1 | 5/2014 |
| WO | 2014145338 A1 | 9/2014 |
| WO | 2014149865 A1 | 9/2014 |
| WO | 2014163706 A1 | 10/2014 |
| WO | 2014194178 A1 | 12/2014 |
| WO | 2015004624 A1 | 1/2015 |
| WO | 2015004625 A1 | 1/2015 |
| WO | 2015057407 A1 | 4/2015 |
| WO | 2015077274 A1 | 5/2015 |
| WO | 2016002189 A1 | 1/2016 |
| WO | 2016004137 A1 | 1/2016 |
| WO | 2016016899 A1 | 2/2016 |
| WO | 2017006510 A1 | 1/2017 |
| WO | 2017035487 A1 | 3/2017 |
| WO | 2018000333 A1 | 1/2018 |
| WO | 2018213209 A1 | 11/2018 |
| WO | 2022002054 A1 | 1/2022 |
| WO | 2023006048 A1 | 2/2023 |
| WO | 2023076103 A1 | 5/2023 |
| WO | 2023081236 A1 | 5/2023 |
| WO | 2023091769 A1 | 5/2023 |
| WO | 2023096804 A1 | 6/2023 |
| WO | 2023154250 A1 | 8/2023 |
| WO | 2023196150 A1 | 10/2023 |
| WO | 2023244454 A1 | 12/2023 |
| WO | 2023244767 A1 | 12/2023 |
| WO | 2023250114 A1 | 12/2023 |
| WO | 2024001789 A1 | 1/2024 |
| WO | 2024003620 A1 | 1/2024 |
| WO | 2024007575 A1 | 1/2024 |
| WO | 2024009540 A1 | 1/2024 |
| WO | 2024010739 A1 | 1/2024 |
| WO | 2024030520 A1 | 2/2024 |

OTHER PUBLICATIONS

Al-Khaja et al., "Eleven years' experience with Carpentier-Edwards biological valves in relation to survival and complications", European Journal of Cardio-Thoracic Surgery, vol. 3, No. 4, pp. 305-311, Jul. 1, 1989, Springer-Verlag, Berlin, Germany.

Almagor et al., "Balloon Expandable Stent Implantation in Stenotic Right Heart Valved Conduits", Journal of the American College of Cardiology, vol. 16, No. 5, pp. 1310-1314, Nov. 15, 1990.

Andersen, et al., "Transluminal implantation of artificial heart valves. Description of a new expandable aortic valve and initial results with implantation by catheter technique in closed chest pigs", European Heart Journal, vol. 13, No. 5, pp. 704-708, May 1, 1992, The European Society of Cardiology, Oxford University Press, United Kingdom.

Andersen, H.R. "History of Percutaneous Aortic Valve Prosthesis," Herz, vol. 34., No. 5, pp. 343-346, Aug. 2009, Urban & Vogel, Germany.

Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as Jun. of 2014.

Banai, Shmeul et al., The Journal of the American College of Cardiology, "Transapical Mitral Implantation of the Tiara Bioprosthesis Pre-Clinical Results," Feb. 2014, <http://interventions.onlinejacc.org/article.aspx?articleid=1831234>.

Benchimol et al., "Simultaneous left ventricular echocardiography and aortic blood velocity during rapid right ventricular pacing in man", The American Journal of the Medical Sciences, vol. 273, No. 1, pp. 55-62, Jan.-Feb. 1977, Elsevier, United States.

Berreklouw, Eric, PhD, et al., "Sutureless Mitral Valve Replacement With Bioprostheses and Nitinol Attachment Rings: Feasibility in Acute Pig Experiments," The Journal of Thoracic and Cardiovascular Surgery, vol. 142, No. 2, Aug. 2011 in 7 pages, Applicant believes this may have been available online as early as Feb. 7, 2011.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, No. 30, pp. 654-670, Nov. 1, 1964, Lippincott Williams & Wilkins, Philadelphia, PA.

Inoune et al., "Clinical application of transvenous mitral commissurotomy by a new balloon catheter," The Journal of Thoracic and Cardiovascular Surgery, vol. 87, No. 3, pp. 394-402, Mar. 1984, Elsevier, United States.

Kolata, Gina "Device That Opens Clogged Arteries Gets a Failing Grade in a New Study", The New York Times, Jan. 3, 1991, pp. 1-2 [online], [retrieved on Jul. 29, 2009]. Retrieved from the Internet <URL:http://www.nytimes.com/1991/01/03/health/device-that-opens-clogged-arteries-gets-a-faili . . . .

Lawrence, Jr., et al., "Percutaneous Endovascular Graft: Experimental Evaluation", Cardiovascular Radiology 163, pp. 357-360, May 1987.

Pavcnik et al., "Development and Initial Experimental Evaluation of a Prosthetic Aortic Valve for Transcatheter Placement," Radiology, vol. 183, No. 1, pp. 151-154, Apr. 1, 1992. Elsevier, United States.

Porstmann et al., "Der Verschluß des Ductus Arteriosus Persistens Ohne Thorakotomie", Thoraxchirurgie Vaskulare Chirurgie, Band 15, Heft 2, Stuttgart, im Apr. 1967, pp. 199-203.

Sabbah et al., "Mechanical Factors in the Degeneration of Porcine Bioprosthetic Valves: An Overview", Journal of Cardiac Surgery, vol. 4, No. 4, pp. 302-309, Dec. 1989.

Selby et al., "Experience with New Retrieval Forceps for Foreign Body Removal in the Vascular, Urinary, and Biliary Systems", Radiology, vol. 176, No. 2, pp. 535-538, Jul. 31, 1990, Radiological Society of North America, Oak Brook, IL.

Serruys et al., "Stenting of coronary arteries. Are we the sorcerer's apprentice?", European Heart Journal, vol. 10, No. 9 pp. 774-782, Sep. 1, 1989, The European Society of Cardiology, Oxford University Press, United Kingdom.

Sigwart, Ulrich, "An Overview of Intravascular Stents: Old and New," Textbook of Interventional Cardiology, Second Edition, chapter 48, pp. 803-815, © 1994, W.B. Saunders Company, Philadelphia, PA.

Uchida et al., "Modifications of Gianturco Expandable Wire Stents", Technical Note, American Roentgen Ray Society, pp. 1185-1187, May 1988.

Urban, Philip MD, "Coronary Artery Stenting", pp. 5-47, © 1991, ISBN: 2-88049-054-5, Editions Medecine et Hygiene, Geneva, Switzerland.

(56) References Cited

OTHER PUBLICATIONS

Watt et al., "Intravenous adenosine in the treatment of supraventricular rachycardia: a dose-ranging study and interaction with dipyridamole", British Journal of Clinical Pharmacology, vol. 21, No. 2, pp. 227-230, Feb. 1986, British Pharmacological Society, London, United Kingdom.

Wheatley, David J., "Valve Prosthesis", Rob & Smith's Operative Surgery—Cardiac Surgery, vol. 91, No. 2, pp. 415-424, Feb. 1, 1987, Butterworth Scientific, London, UK.

\* cited by examiner

TRANSCATHETER PROSTHETIC HEART VALVE AND DELIVERY SYSTEM

CROSS REFERENCE TO RELATED APPLICATIONS

This application is a continuation of U.S. application Ser. No. 16/740,916, filed Jan. 13, 2020, now U.S. Pat. No. 11,559,395, which is a continuation of U.S. application Ser. No. 15/526,810, filed May 15, 2017, now U.S. Pat. No. 10,531,951, which is a U.S. National Stage entry of International Application No. PCT/EP2015/077856, filed on Nov. 26, 2015, which claims priority to Greek Patent Application No. 20140100595, filed on Nov. 26, 2014, each of which is hereby incorporated by reference herein in its entirety.

FIELD OF THE INVENTION

The invention generally relates to devices for cardiovascular treatment. More specifically, the invention generally relates to devices for percutaneous heart valve replacement/implantation.

BACKGROUND OF THE INVENTION

Valvular heart disease is common and involves considerable mortality and morbidity. Surgical replacement of the failing valve is the treatment of choice when the disease progresses and certain criteria are fulfilled. However, it is not uncommon patients fulfilling the criteria for this treatment to be rejected due to a perceived unacceptably high surgical risk for a variety of reasons such as advanced age and comorbidities. For some it is their decision to deny this treatment. These factors drove the development of prosthetic heart valve devices that can be implanted percutaneously with guiding catheters. Many such devices for the treatment of aortic valve stenosis have gained regulatory approvals and are already successfully and widely used offering clinical and survival benefits in many patients. Recently, we have seen the first device gaining regulatory approval for the percutaneous treatment of aortic valve insufficiency.

Aortic and mitral valve disease (stenosis and/or insufficiency) are equally common but despite the success in developing percutaneous prosthetic valves for the aortic valve, developing a device for percutaneously replacing the mitral valve have been challenging and problematic. The main reason is the much more complex and uneven anatomy of the mitral valve.

Apparently, the development of such a device for the percutaneous replacement of the mitral valve would be of great benefit for many patients.

This invention provides numerous alternative solutions to overcome these problems and develop a successful percutaneously delivered prosthetic mitral valve. Some of the solutions described could be used for similar prosthetic devices for implantation in other heart valves.

SUMMARY OF THE INVENTION

The invention relates to a prosthetic heart valve for an endoprosthesis used in the treatment of a stenotic heart valve and/or a heart valve insufficiency. The prosthetic heart valve comprises a plurality of leaflets, which consist of a natural and/or synthetic material and are being able to switch between their open and close position in response to the blood flow through the heart. The leaflets are attached into a collapsible wire valve frame involving a stent part and a wire mesh part that complement each other in many ways. The frame has a body that defines a lumen to its inside. The exterior portion of the frame has features that serve for its conformation and stabilization/anchoring in the anatomic structures it contacts. When the endoprosthesis apparatus is expanded within the intended failing native heart valve it replaces it and resumes its function.

The endoprosthesis is contained in a sheathed capsule and is inserted into the body and advanced to the intended location with a delivery system for percutaneously deploying a prosthetic heart valve. This system apart from the sheathed capsule includes an inner shaft assembly, and a handle maintaining control knobs that enable independent movement of the various parts of the sheathed capsule and the endoprosthesis. The handle functions allow for gradual release and deployment of the endoprosthesis, but also can recapture the endoprosthesis and safely remove it out of the body even after its complete deployment to its full functional status.

DETAILED DESCRIPTION OF THE INVENTION

Transcatheter Mitral Valve

Figure 1:
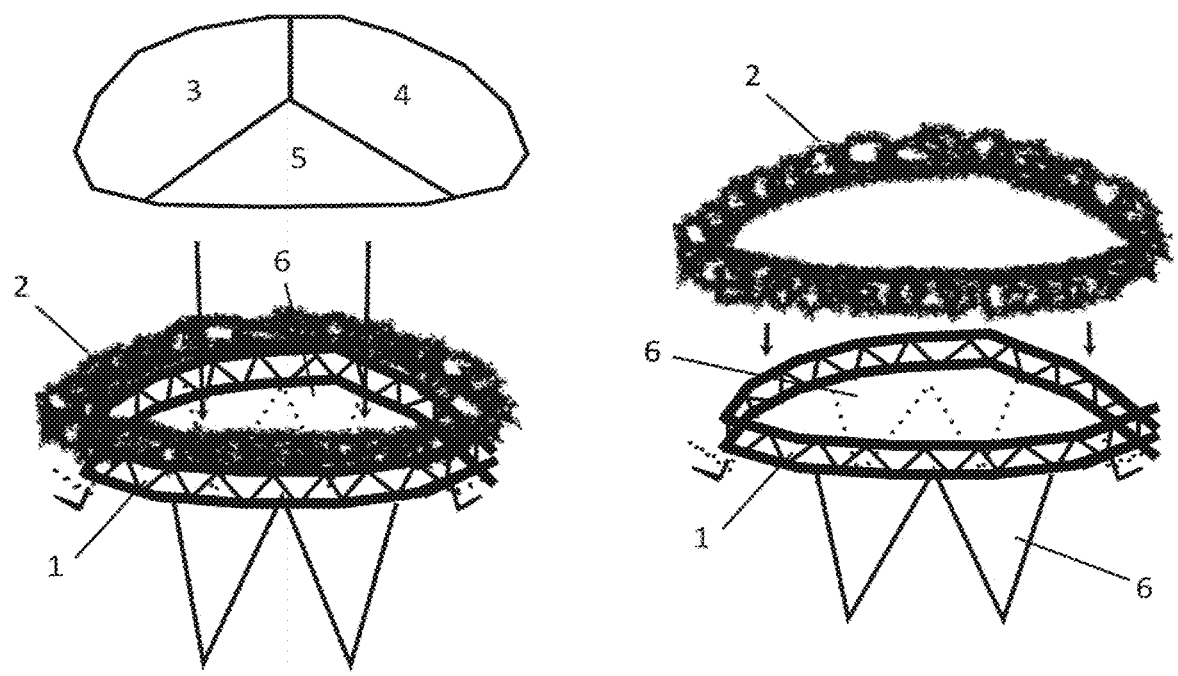
FIG. 1 shows a first embodiment of a prosthetic valve according to the present invention.

This prosthetic heart valve and its delivery system are intended for use in the treatment of mitral valve insufficiency and/or mitral valve stenosis. The delivery method is retrograde (the approach of the diseased mitral valve is achieved from within the left ventricle-transapical access and against the flow of the blood) or antegrade (the approach of the diseased mitral valve is achieved from within the left atrium after direct surgical approach or transeptal puncture and along with the flow of the blood), with the use of specifically designed for each access delivery systems.

The endoprosthesis comprises of a plurality of leaflets attached to a collapsible wire frame. This frame integrates a stent part and a braided and/or flat wire mesh part that complement each other in many ways. The combination of these two different resources in building the frame of the transcatheter valves described in this invention is very important and it is believed to solve many of the problems encountered to date for the development of a successful percutaneous prosthetic mitral valve. The stent part towards its ventricular end and the wire mesh part towards its atrial end. The wire mesh surrounds the stent at the atrial end and forms a body around the stent extending beyond the atrial end. According to certain embodiments of the present invention, the wire mesh extends also longitudinally towards the ventricular end of the stent forming again a body around the stent. There are limitless combinations of the relative length proportions of the endoprosthesis these parts may occupy, and they may overlap. It can have several standardized shapes and sizes. It can even be custom made based on measurements from the patient's anatomy obtained by medical imaging.

The outer parts of the wire mesh towards the atrium may be braided or flat. The rest of the wire mesh is braided. The stent part that will cover at least the annulus level has a sealing skirt from suitable material. The stent part may be cylindrical or conical (and may have a flaring towards the ventricle in order to withstand the excessive systolic forces exerted on the device with every heart beat). The wire mesh part can incorporate a fabric or other sealing material to make it instantly impermeable.

The stent part may be made of collapsible nitinol, stainless steel or other material and can self-expand. The wire mesh may be made of collapsible nitinol, stainless steel or other material and can self-expand. The advantages of the stent component is that it has maximal radial force and thus can appose and stabilize the frame optimally in areas of the mitral valve this is needed (such as the annulus area). It also provides the areas at which the prosthetic valve leaflets are attached and other structures described later. The wire mesh on the other hand, can better conform and adapt to areas of uneven and unpredictable anatomy and offer optimal sealing of unwanted blood flow by doing so. The shutting of unwanted blood flow can be instant when fabric or other components are incorporated into or on the mesh. The flat wire mesh can expand to larger diameters and reach longer where needed without occupying large volumes. The braided wire mesh may expand less but it self-adjusts perfectly to fill in restrained spaces (such as spaces between the mitral valve annulus and the stent part of the frame) and to assume the shape of the anatomy it apposes to (such as the mitral valve annulus).

Figure 2:
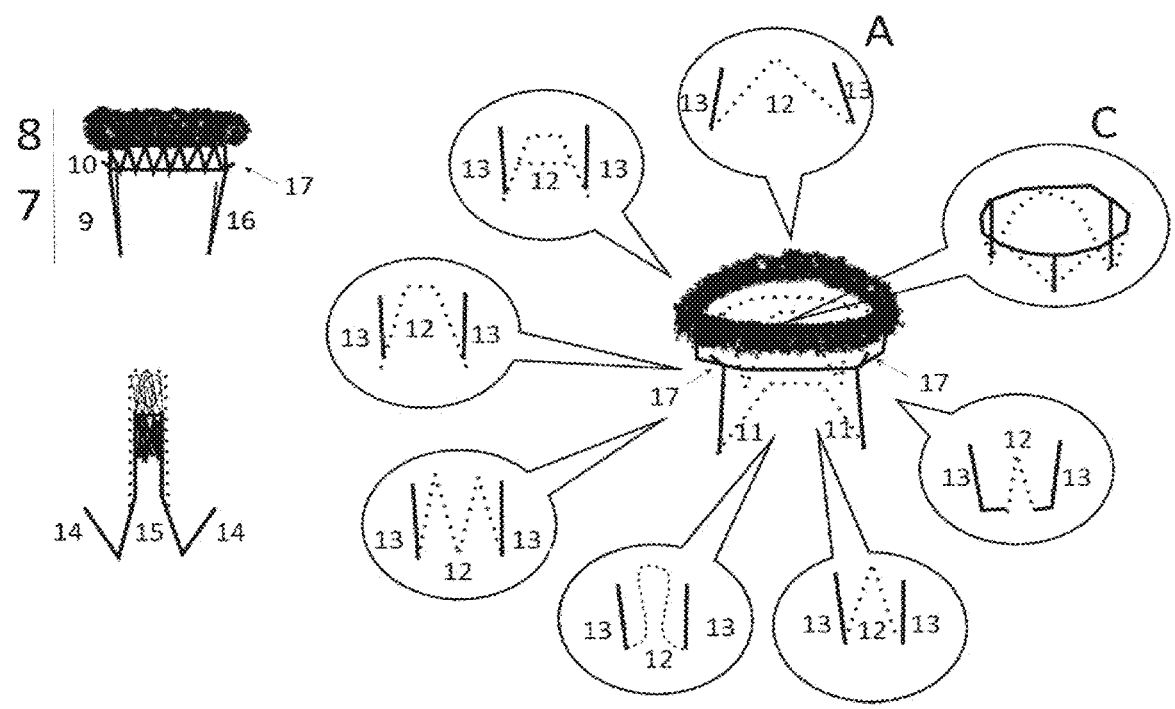
FIG. 2 shows a further embodiment of a prosthetic valve according to the present invention.

The endoprosthesis frame apposes to the intended area and its anatomically designed shape together with its radial strength and its other supporting features allow it to steadily fix. In addition, the frame has particular features on its outer surface that allow deploying the endoprosthesis at the anatomically appropriate area. The frame also allows for degrees of auto-adjustment towards the anatomically appropriate area/plane. Besides the integration of a stent and a wire mesh to form the frame of the endoprosthesis, the second most important feature in the invented solutions presented in the following sections is the provision of particular components of the stent to guide and retain the device to the anatomically correct deployment position by tracking these components behind the native mitral valve leaflets and capturing them wide-open (FIG. 2, 9). These components are referred to as capturing elements. According to a preferred embodiment of the present invention, the capturing elements comprise a part that extends radially beyond the body of the wire mesh which surrounds the stent.

The valve leaflets can consist of a natural and/or synthetic material and are being able to switch between their open and close position in response to the blood flow through the mitral valve. Their fixed sides are seamed or attached with other means at the wire frame of the endoprosthesis (such as the stent ring end and the interior native valve leaflet enveloping elements). They start to function when the wire mesh part of the endoprosthesis is released.

The delivery catheter comprises a distal capsule that contains the endoprosthesis at its compressed state and the catheter shaft assembly that extends from within the capsule to the outer system handle. The handle maintains control knobs and/or dials and/or buttons that are connected to layers of the shaft assembly that on their other end within the capsule function to gradually open the capsule and uncover the endoprosthesis. This causes the uncovered parts of the latter to assume their default-uncompressed state and shape, allowing the inner lumen of the frame to form and the valve leaflets to commence function propelled by the blood flow. The handle also maintains functions that allow through shaft layers and or other components to resheath and remove the endoprosthesis even after full delivery and function is achieved.

The device allows for complete atraumatic re-capture/research and removal of the endoprosthesis even after its full deployment and assumption of its function.

DETAILED DESCRIPTION OF THE EMBODIMENTS

Embodiment 1

FIG. 1 shows a first embodiment of a prosthetic mitral valve according to the present invention comprising a stent (1) and a wire mesh (2) surrounding the stent at the atrial end and forming a body around the stent (2) which extends beyond the atrial end. The stent comprises internally three valve leaflets (3, 4, 5). Furthermore, the stent forms at its ventricular end a pair of capturing elements (6) which capture the native leaflets thus providing positioning guidance and anchoring/retention.

Embodiment 2

The endoprosthesis (FIG. 2) comprises of a plurality of leaflets, which consist of a natural and/or synthetic material and are being able to switch between their open and close position in response to the blood flow through the heart. The leaflets are attached into a collapsible wire valve frame that includes a stent (7) and a wire mesh (8). The frame has a body that defines a lumen to its inside. The exterior portion of the frame has features that serve for its conformation and stabilization/anchoring in the anatomic structures it contacts. When the endoprosthesis apparatus is expanded within the intended failing native heart valve it replaces it and resumes its function. The frame of the endoprosthesis includes a stent and a wire mesh. All these are also described in the embodiment 1.

The stent part of the endoprosthesis includes a crown (9), and a ring (10). The crown includes capturing elements for each of the native valve leaflets (11). Each such element has an exterior (12) and an interior part (13) for enveloping/capturing/clipping the respective native valve leaflet. The first component of the stent that expands within the left ventricle is the part of the crown that has at least two external wings/hooks/clipping elements (14), also shown in FIG. 3A, 3B, which are the first to appear when the ventricular part of the capsule starts to open towards the apex of the ventricle. Once released, they are fully expanded. Their expansion ("opening") is achieved by the default design of the frame as they exit the sheath and possibly from special features at their articulation to the rest of the frame (such as thicker areas of the struts close to the articulation that push away the external elements when released, but as the frame opens these areas do not overlap anymore and the external elements come close again to their internal counterparts to clip the leaflets).

These external elements when released are aligned using continuous real-time imaging modalities, such as transesophageal echocardiography, to extend behind (outside) each of the two native mitral valve leaflets. At the same time the tips of the interior enveloping/capturing/clipping elements start to flare (15) when the ventricular side of the capsule opens to fully release their outer counterparts. Once this is achieved the entire system is moved so that the tips of the exterior wings/hooks/clipping elements approach and contact the mitral valve annulus at its ventricular side. It is expected that when this occurs the operator will experience resistance providing tactile feedback for the correct positioning. During this initial phase the native mitral valve function is uninterrupted. The exterior elements by sitting behind the leaflets and reaching deep into the annulus create an anchoring of the entire frame on the ventricular side of the mitral annulus.

Then, and while exerting a steady force to keep the external wings/hooks/clipping parts at or as close as possible to the ventricular side of the mitral annulus, the atrial side of the capsule opens releasing the rest of the endoprosthesis frame.

The first to be released next is the part of the stent crown that holds the bases of the internal enveloping/capturing/clipping elements. These expand towards their external counterparts and capture/envelop/clip the native valve leaflets locking them into a wide-open position by doing so. By pairing these hooking components on either side of the native valve leaflets these are engulfed/enveloped/clipped in between them and as the frame keeps expanding they are locked in this position. The interior pairing constituents (13) have sufficient length to capture at least the tips of the native leaflets before they join the stent ring. They may also be made to have a progressively greater default expansion towards the annulus (16) than their exterior counterparts, and by doing so they fix the native valve leaflets actively inside (essentially by clipping them). The pairing components can have a range of shapes that pinch the native leaflets in between (12, 13). Furthermore, the capture elements of the anterior and posterior native valve leaflets may differ in shape to match the different anatomy of these leaflets. For example, the exterior elements of the anterior leaflet may be wider and longer than their interior counterparts and have a reversed M shape so that their two bases are seated closer to the fibrous trigones on both sides of the anterior leaflets (FIG. 2A).

After the stent crown is released and the native valve leaflets are locked wide open in it, the ring of the stent is released. The stent ring has a fabric skirt layer attached for sealing the areas of the annulus it apposes to from unwanted blood flow. The shape of the ring may be rather oval and in any case resembling and conforming optimally with the shape of the mitral valve annulus. Externally it may have anchoring elements such as hooks, barbs, spikes, indentations or similar (17) to secure on the annulus as it apposes against it, and provide additional stabilization of the endoprosthesis at the annulus on this occasion. These anchoring features are mainly found towards the perimeter of the stent that apposes to the commissural areas of the annulus. Maximal radial strength is given at the larger diameter of the stent. The radial strength of the stent arc that apposes the annulus at the root of the anterior leaflet is calculated so that it does not push the leaflet into the outflow tract of the left ventricle and cause obstruction. For the same reason, the clipping mechanism of the anterior leaflet when fully expanded may have an incline away from the outflow tract.

In the interior part of the stent ring there are elements for passively attaching the endoprosthesis on its delivery catheter pins during the crimping process. This passive attachment offers stabilization of the endoprosthesis on its delivery catheter while the capsule components move to release various parts of it, till of course the capsule uncovers the area of the stent ring that sits on the catheter pins and releases it.

The prosthetic valve leaflets are attached to the stent ring and the interior enveloping elements of the stent crown but can also be attached at other purposely-devoted posts of the stent (FIG. 2C).

Lastly, the wire mesh part of the endoprosthesis (8) is released by continued opening of the atrial side of the capsule (FIG. 3C, 3D). This consists of a rather oval shaped (that in any case resembles the anatomy of the annulus) thin wire mesh that can incorporate a fabric or other material to make it instantly impermeable. It is attached and is the continuation of the most atrial side of the stent. When released, it expands from the native valve annulus overlapping with the stent towards the surrounding atrial walls. It has sufficient length to extent enough into the atrial side of the mitral valve annulus. By doing so stabilizes the endoprosthesis at the atrial level of the annulus and allows auto-adjustment of the entire endoprosthesis. It has a progressively larger default diameter than the atrial side of the stent, and it may be made to have a tendency to revert backwards and appose actively to the atrial wall on the atrial side of the annulus and above it offering superior sealing from paravalvular insufficiency and improving the stabilization of the entire frame. The length of the wire mesh ring can differ locally to conform best to the anatomy it apposes to. The entire mesh wire can be braided. Alternatively, the most exterior parts of the wire mesh that are away from the annulus can be made of flat mesh, while as it comes closer to the annulus it becomes braided.

In summary, all segments offer the stabilizing mechanism of this endoprosthesis. The stent crown of the frame contains the paired elements that actively capture, envelope and lock wide open the two native valve leaflets. In addition, the bases of the exterior elements are behind the native leaflets and are immobilized by the ventricular side of the annulus. This latter segment offers also tactile feedback for the correct positioning of the endoprosthesis.

The stent ring expands and apposes the native valve annulus and has also special features for anchoring on it. Finally, the wire mesh offers stabilization at the level of the annulus and towards the atrial side and locks the endoprosthesis at its final position, offering at the same time room for self-adjustment and self-alignment.

The release of this endoprosthesis starts from the ventricle and ends in the left atrium.

The endoprosthesis can have several standardized shapes and sizes. It can even be custom made based on measurements from the patient's anatomy obtained by medical imaging.

The resheath/recapture/removal capability of the endoprosthesis, even after complete deployment, is described in the delivery catheter section.

Embodiment 3

Figure 4:
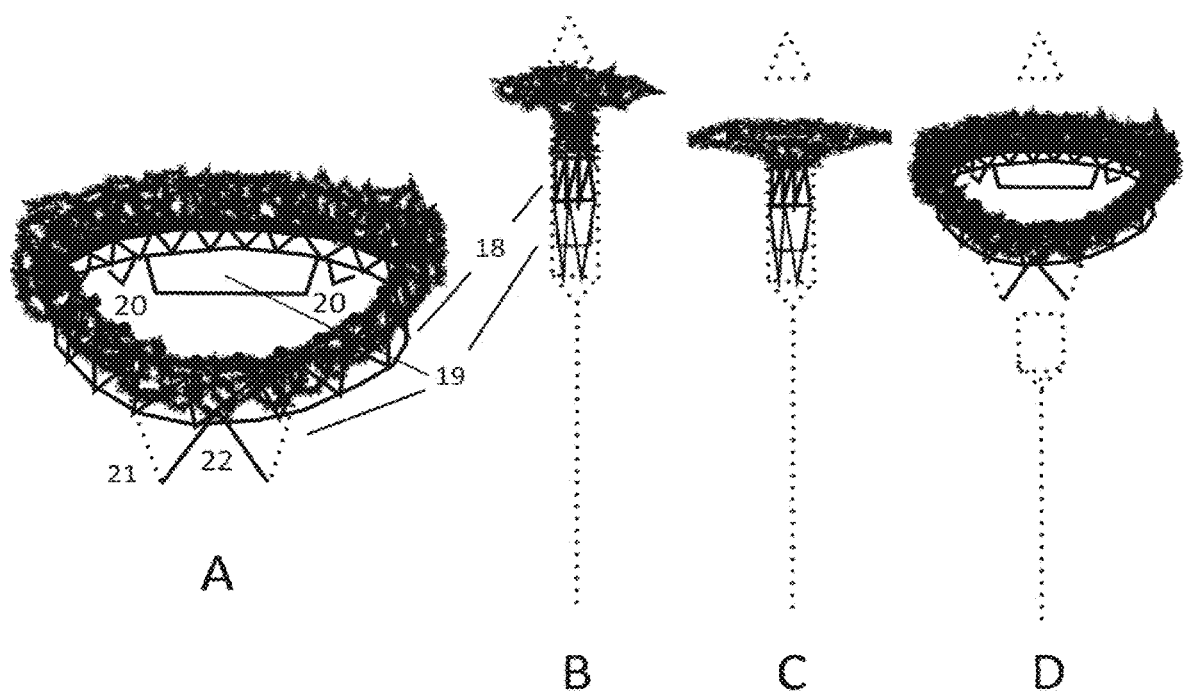
FIG. 4 shows another embodiment of a prosthetic valve according to the present invention.

Another version (FIG. 4A) of the described in the embodiment 2 endoprosthesis can be deployed in the opposite way, starting from the atrial side (FIG. 4B, 4C, 4D). First, the wire mesh is gradually released within the left atrium (FIG. 4B, 4C). The valve then is pulled downward till the wire mesh seats firmly at the floor of the atrium. Then the stent ring (18) is released followed by its crown (19) that contains a plurality of anchoring structures (hooks, barbs, spikes, indentations or similar) (20) extending into the ventricular side of the annulus. Two of them may be seated and capture the fibrous trigones on both sides of the anterior leaflet and hold this leaflet wide-open. Another component of the crown may extend in the middle part of the posterior leaflet (21). This is longer and therefore the last to be completely released from the delivery system. Its final part folds completely backwards (22) towards the ventricular side of the annulus to capture the posterior leaflet.

The elements for passively attaching of this endoprosthesis on its delivery catheter pins during the crimping process are at the most ventricular tips of the stent crown. This is the part of the endoprosthesis released last. This passive attachment offers steadiness of the endoprosthesis on its delivery catheter while the capsule components move to release various parts of it, till of course the capsule uncovers this final part.

The endoprosthesis can have several standardized shapes and sizes. It can even be custom made based on measurements from the patient's anatomy obtained by medical imaging. The prosthetic valve leaflets are attached to the stent ring and the interior enveloping elements of the stent crown but can also be attached at other areas of the wire frame.

Embodiments 4 a,b

Figure 5:
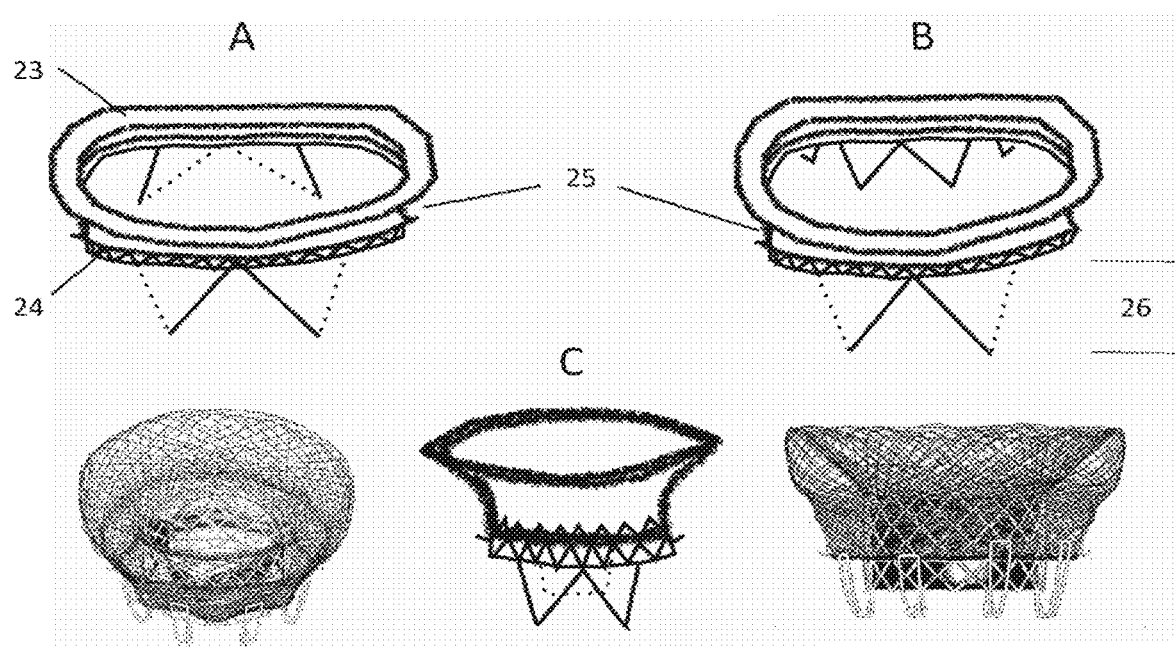
FIG. 5 shows another embodiment of a prosthetic valve according to the present invention.

Another version of either of the two previous embodiments (2 and 3) can have a more dominant wire mesh part that alone or with a degree of overlap with the stent part apposes at the annulus and succeeds the stabilization of this endoprosthesis (FIG. 5). In the previous two versions it was mainly the stent ring of the frame to be apposed and seated at the annulus level. In this version the wire mesh (23) occupies a larger length of the frame of the endoprosthesis and allows it to well reach and appose in the annulus. The stent part (24) is mostly below the annulus (FIG. 5A, 5B) but may also reach the level of the annulus and overlap internally the wire mesh (FIG. 5C).

The wire mesh of this endoprosthesis covers from just below the annulus, then covers it and extends at the surrounding atrial walls. It has a trench or channel or concavity at its outer perimeter (25) that has the shape of the annulus and slightly oversizes it, so that by expanding on the annulus sits on its both sides fixing perfectly and steadily the endoprosthesis.

The stent part in this case, connects to the wire mesh below the annulus and it is shorter. Alternatively, it may have a component to surround the wire mesh away from its outer perimeter (internally) at the level of the annulus and provide additional radial force to it (FIG. 5C). Then it has a crown part extending towards the left ventricle (26) with elements to hold or capture the native valve leaflets wide open. The stent crown can be similar to embodiment 2, and in this case the ventricular part of the endoprosthesis is first deployed allowing for capturing the native valve leaflets, self-positioning below the annulus and anchoring and stabilization at the ventricular side. Then the rest of the stent and the wire mesh are deployed (embodiment 4a) (FIG. 5A).

The stent crown can also be similar to embodiment 3, and in this case the atrial part of the endoprosthesis is first deployed and pulled downward till the wire mesh seats firmly at the floor of the atrium. Then the rest of the wire mesh is deployed surrounding the annulus and finally the stent parts that hold or capture the native valve leaflets wide-open and offer additional anchoring and stabilization at the ventricular side (embodiment 4b) (FIG. 5B).

The wire mesh incorporates a fabric or other material to make it instantly impermeable and may have a fabric skirt at the level of the annulus for better sealing. The endoprosthesis can have several standardized shapes and sizes. It can even be custom made based on measurements from the patient's anatomy obtained by medical imaging.

The prosthetic valve leaflets are attached to the wire frame of the endoprosthesis at the stent part.

Embodiment 5

Figure 6:
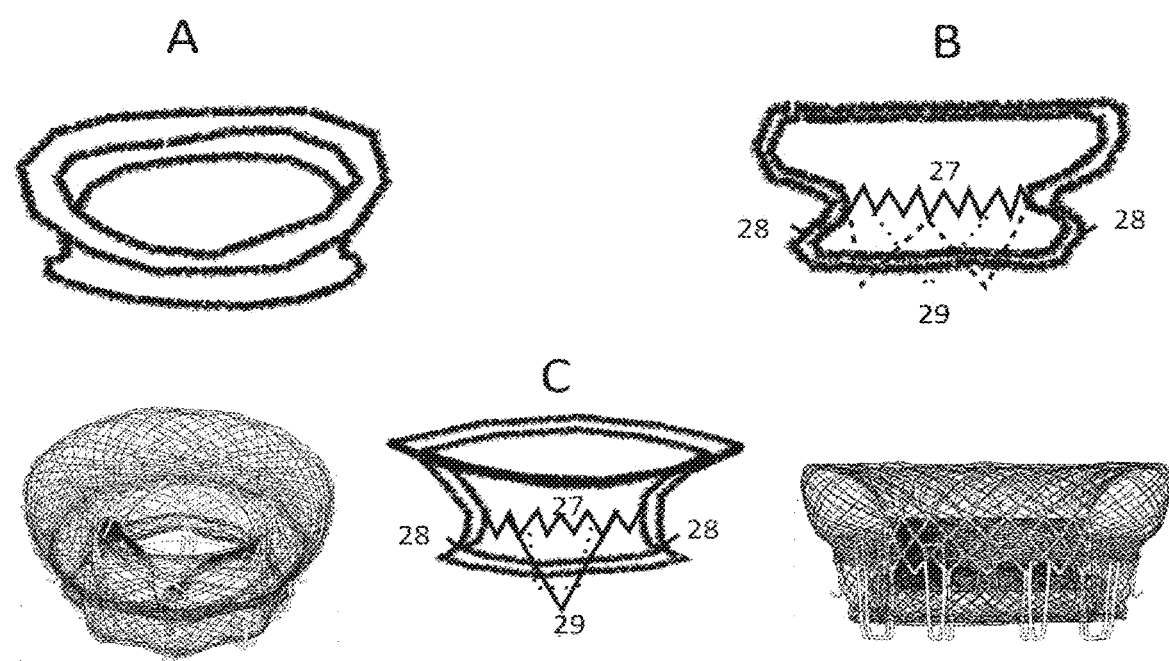
FIG. 6 shows another embodiment of a prosthetic valve according to the present invention.

This version is similar to the previous embodiment 4, but the frame of this endoprosthesis is entirely formed by the wire mesh (FIG. 6).

The atrial side is first released within the left atrium. The valve then is pulled downward till the wire mesh seats firmly at the floor of the atrium. By doing so stabilizes the endoprosthesis at the atrial level of the annulus and allows auto-adjustment of the entire endoprosthesis. It has a progressively larger default diameter at its atrial side, and it may be made to have a tendency to revert backwards and appose actively to the atrial wall on the atrial side of the annulus and above it offering superior sealing from paravalvular insufficiency and improving the stabilization of the entire frame. The dimensions of the wire mesh can differ locally to conform best to the anatomy it apposes to. The entire mesh wire can be braided. Alternatively, the most exterior parts of the wire mesh that are away from the annulus can be made of flat mesh, while as it comes closer to the annulus it becomes braided. The wire mesh incorporates a fabric or other material to make it instantly impermeable. It can also have a fabric skirt at the level of the annulus for better sealing.

Then by keeping the opened atrial part on the floor of the atrium the part that apposes at the annulus is released. This has a trench or channel or concavity at its outer perimeter that has the shape of the annulus and slightly oversizes it, so that by expanding on the annulus it sits on its both sides fixing perfectly and steadily the endoprosthesis.

The wire mesh extends more into the surrounding atrial walls than in the ventricular side of the annulus (FIG. 6A). The shape and dimensions of the atrial and ventricular parts of the mesh are such to appose comfortably at their intended locations.

This endoprosthesis wire mesh frame may have one or more of the additional components: A. A collapsible wire component, such a short stent, to surround the wire mesh internally at the level of the annulus and to provide additional radial force to it at that level (27). B. Stand-alone or connected wire elements (hooks, barbs, spikes, indentations or similar) at the outer ventricular surface of the frame for anchoring below the annulus (28). C. Particular wire posts and elements for attachment of the prosthetic leaflets and for holding the native valve leaflets wide open (29).

The wire mesh incorporates a fabric or other material to make it instantly impermeable and may have a fabric skirt at the level of the annulus for better sealing. The endoprosthesis can have several standardized shapes and sizes. It can even be custom made based on measurements from the patient's anatomy obtained by medical imaging.

The prosthetic valve leaflets are attached to the wire frame of the endoprosthesis. This endoprosthesis can be deployed either from its atrial or its ventricular side.

Embodiment 6

Figure 7:
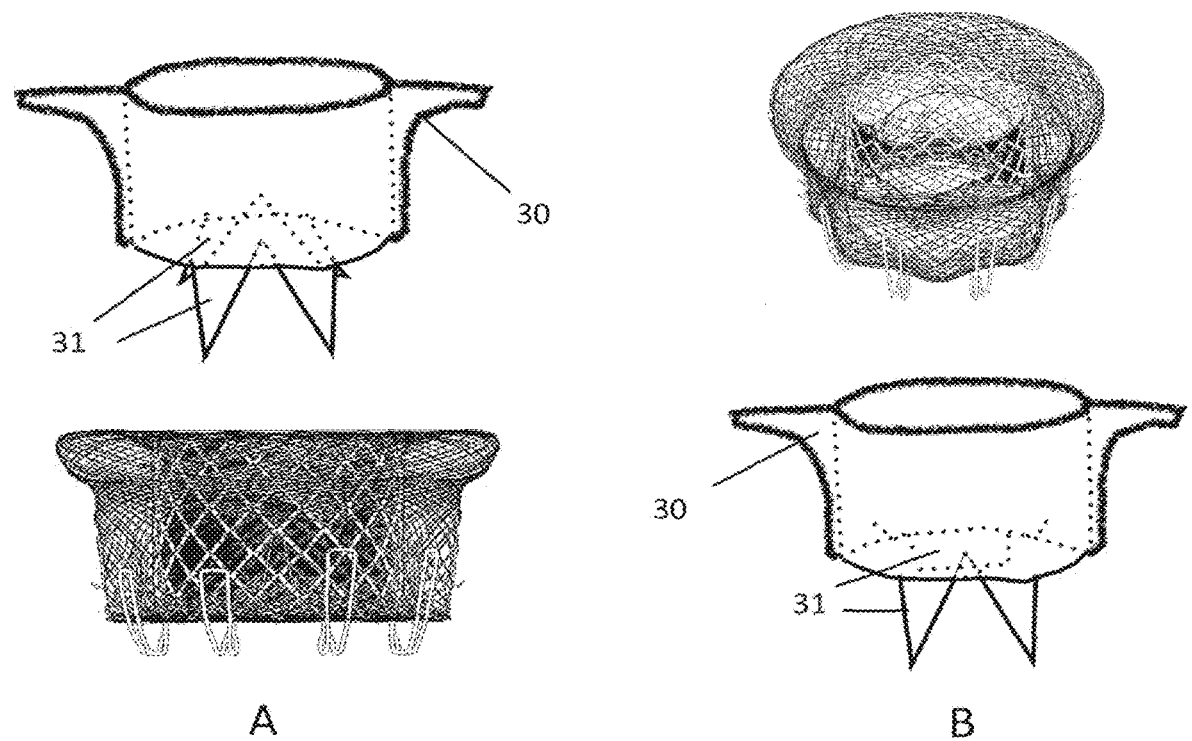
FIG. 7 shows another embodiment of a prosthetic valve according to the present invention.

This embodiment describes an endoprosthesis, which is a version of either the embodiments 2-4 endoprosthesis. The main feature of this version that makes it distinct from those embodiments is that the stent part of the endoprosthesis frame is dominant and occupies the majority or the entire length of the frame, with the wire mesh part being exterior to it forming a body around it (FIG. 7A). The lumen of the endoprosthesis is therefore defined completely by the stent, which is fully surrounded by the wire mesh.

The wire mesh (30) default shape and dimensions are to out-expand the mitral valve annulus towards the atrium to allow the seating, sealing and stabilization of the endoprosthesis at its atrial side. Then the wire mesh continues as a band surrounding the stent at the annulus area and may reach just below it. This part of the wire mesh seals the endoprosthesis at the annular level. It allows the stent to appose within it and compresses on the surrounding tissues offering an optimal adaptation and stabilization at this level.

The dominant stent part in this embodiment takes advantage of the greater radial strength the stent provides to the entire frame and it allows for the formation of a uniform and assured lumien throughout the frame. The skirted stent reaches below the annulus but is short of the tips of the leaflets and its surrounding wire mesh seals any anatomical asymmetries.

The ventricular end of the stent comprises capturing elements (31) that offer stabilization of the endoprosthesis at the ventricular side and holding and capturing the native valve leaflets wide open.

In case the crown of this endoprosthesis is similar to embodiments 2 or 4a, the endoprosthesis is guided and navigated through the ventricle to capture/envelope the native mitral valve leaflets and then the rest of the endoprosthesis is expanded towards the atrium (embodiment 6a) (FIG. 7A).

In case the crown of this endoprosthesis is similar to embodiment 3 or 4b, the endoprosthesis is deployed from the atrium down to the lest ventricle, expanding the crown elements that trap the native mitral leaflets wide open and offer anchoring on the ventricular side of the annulus (embodiment 6b) (FIG. 7B).

The wire mesh incorporates a fabric or other material to make it instantly impermeable and may have a fabric skirt at the level of the annulus for better sealing. The stent part that is not covered by the mesh wire is skirted with a material so blocking any blood flow through its cells/struts. The endoprosthesis can have several standardized shapes and sizes. It can even be custom made based on measurements from the patient's anatomy obtained by medical imaging.

The prosthetic valve leaflets are attached to the stent of the endoprosthesis.

This endoprosthesis can be deployed either from its ventricular (embodiment 6a) or its atrial side (embodiment 6b).

Embodiment 7

Figure 8:
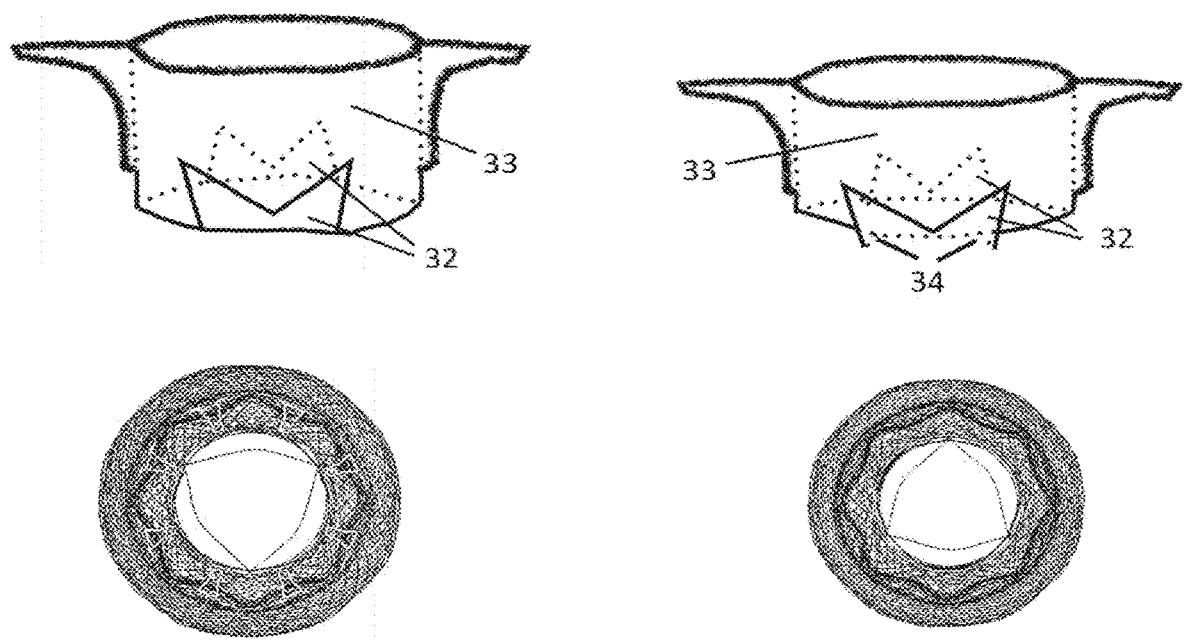
FIG. 8 shows another embodiment of a prosthetic valve according to the present invention.
Figure 9:
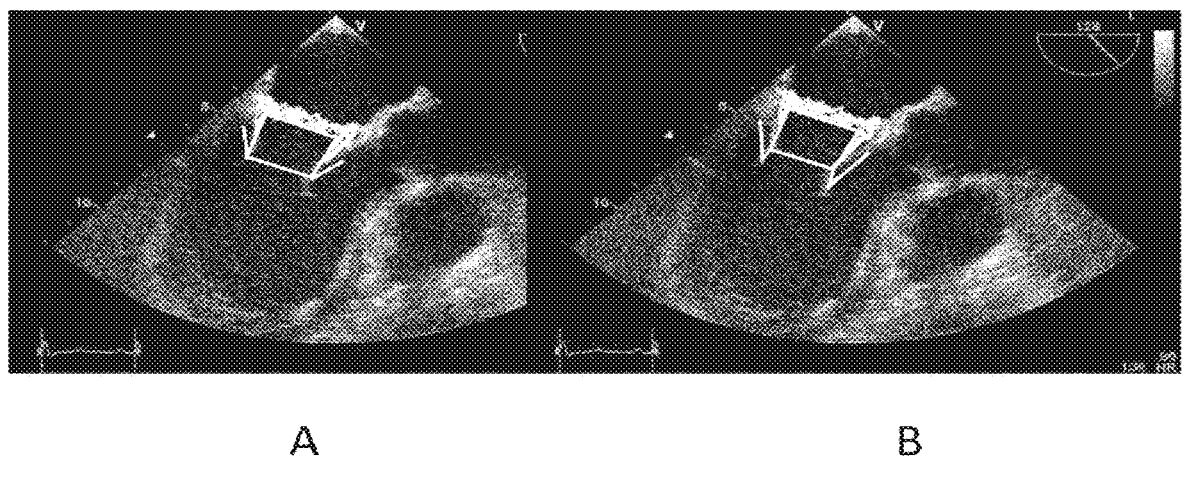
FIG. 9 shows the positioning of a prosthetic valve according to the present invention in a patient's heart.

This embodiment describes an endoprosthesis, which is a version of the embodiment 6 endoprosthesis. The main feature of this version that makes it distinct is that the interior capturing elements of the native mitral valve leaflets is the stent ring itself rather than parts of its crown (FIG. 8, FIG. 9A).

The crown of the stent comprising the exterior capturing elements (32) that provide navigational guidance for the positioning and the stabilization of the endoprosthesis at the ventricular side of the mitral valve annulus (first step of deployment). They expand outside of the native leaflets and as the endoprosthesis is pushed upwards and towards the annulus they are captured by these elements. Then, by continuing the delivery of the endoprosthesis the next part of it expanding is the stent ring itself (33) that apposes against the leaflets from their interior surface. When this occurs the native valve leaflets are captured between the stent and the its external capturing elements. Then the rest of the endoprosthesis is released. This has a thin wire mesh band expanding at the level of the annulus. The wire mesh then outexpands the annulus at its atrial side offering sealing and stabilization. The most ventricular end of the stent may be wire mesh-free (FIG. 8, FIG. 9B).

The endoprosthesis described is deployed from its ventricular side upwards and towards the atrium (embodiment 7a).

To avoid possible prolapse of the stent into the outflow of the left ventricle, a shorter part of the stent crown and its interior capturing elements (as described in endoprosthesis 6) may be preserved especially in the arc of the annulus that apposes towards the native anterior mitral leaflet (34).

In case the crown of this endoprosthesis is similar to embodiment 3, the endoprosthesis is deployed from the atrium down to the lest ventricle, expanding the crown elements that trap the native mitral leaflets wide open and offer anchoring on the ventricular side of the annulus (embodiment 7b).

The wire mesh incorporates a fabric or other material to make it instantly impermeable and may have a fabric skirt at the level of the annulus for better sealing. The stent part that is not covered by the mesh wire is skirted with a material so blocking any blood flow through its cells/struts.

The endoprosthesis can have several standardized shapes and sizes. It can even be custom made based on measurements from the patient's anatomy obtained by medical imaging.

The prosthetic valve leaflets are attached to the stent of the endoprosthesis.

This endoprosthesis can be deployed either from its ventricular side as described (embodiment 7a) or its atrial side (embodiment 7b).

The Delivery Catheter

1. Retrograde Access (Transventricular/Transapical)

Figure 10:
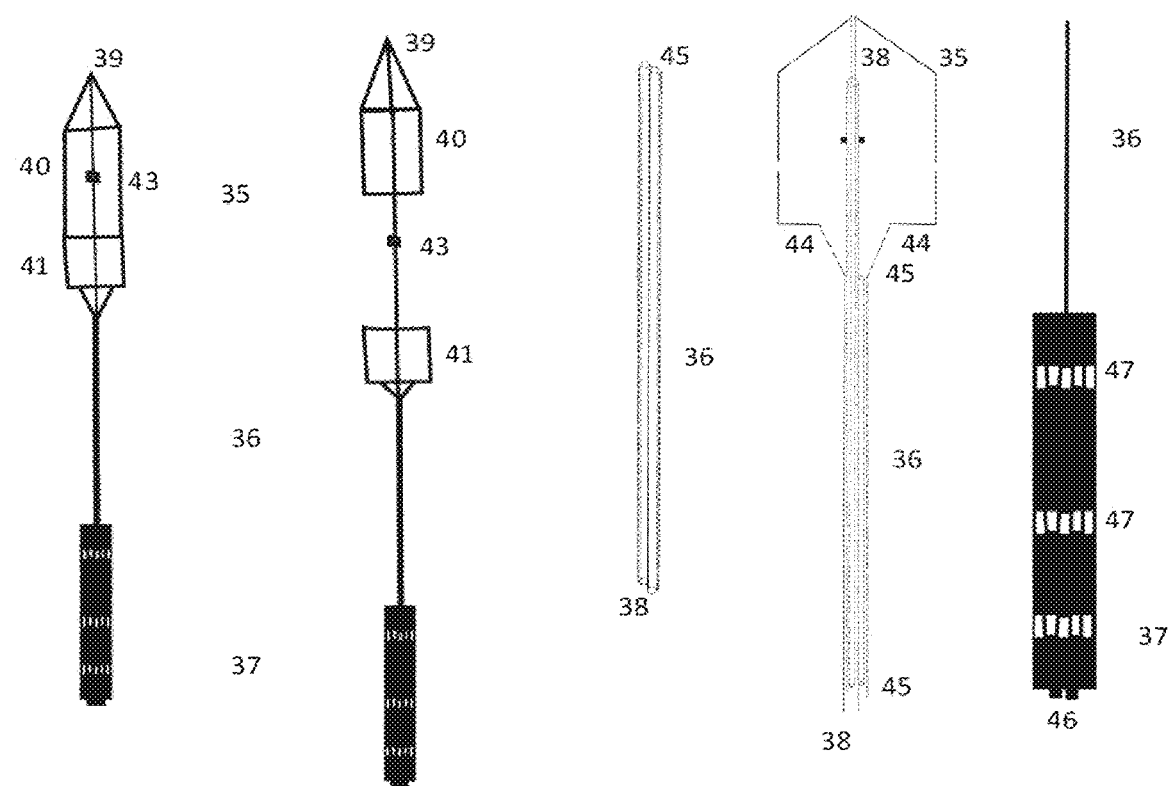
FIG. 10 shows an embodiment of a catheter for the delivery of a prosthetic valve according to the present invention.

The delivery catheter for the endoprosthesis of all embodiments consists of the capsule (FIG. 10,35) that contains the collapsed endoprosthesis, the shaft (36) and the handle (37). They all share a central lumen (38) that accommodates the guide wire over which the device is railed at the intended position of deployment.

The capsule contains the crimped endoprosthesis. Both of its ends are conical (39) to allow smooth tracking.

Figure 3:
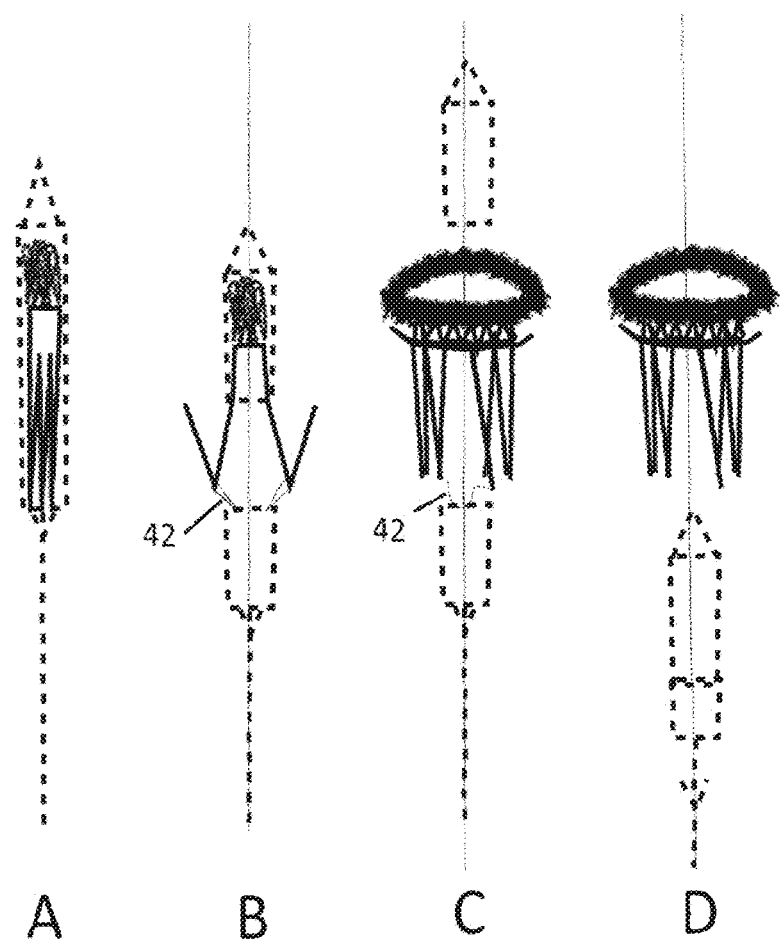
FIG. 3 shows one way of releasing a prosthetic valve according to the invention from its capsule.

For the endoprosthesis of the embodiments 1, 2 and 4a the capsule opens in two parts (FIG. 3, FIG. 10) the atrial part that is longer (40) and the ventricular part that is shorter (41). Each of these parts can move and open/close the respective part of the capsule independently. First the ventricular part is opened (withdrawn/pulled back) the part of the endoprosthesis crimped in this part expands (FIG. 3A, 3B), namely the outside capturing elements of the native valve leaflet expand fully, while their internal counterparts start to flare. When the external capturing/anchoring components are positioned deep behind the native leaflets and if possible in contact to the ventricular side of the annulus, the atrial part of the capsule is opened (advanced/pushed) releasing gradually first the internal native leaflet capturing elements, and then the stent ring and the wire mesh that appose to the annulus and towards the surrounding atrial wall (FIG. 3C, 3D).

When the endoprosthesis is fully deployed and functional it is still connected to the delivery catheter with a plurality of thin wires (such as ultra thin nitinol wires) (42), or screwing wires attached at the most ventricular edge of the stent (area connecting the external and internal capturing elements). Therefore complete atraumatic removal of the endoprosthesis is still feasible. When thin wires are used, they are threaded trough the stent. If the endoprosthesis position and function is satisfactory, one end of the thin wire is pulled till the entire thread is removed from the endoprosthesis and releases it. If the endoprosthesis needs to be removed both ends of the thin wires are pulled together. Another way of reversible connection of the thin wires to the stent is with Highwayman's knots, that allow tightening the knot and tugging by pulling one end of the wire, while the knot unties easily by pulling the other end of the wire.

Finally, an alternative way of attachment is by use of screwing wires that are fixed in female parts found at the stent end.

The part of the shaft traveling inside through the capsule has an inner hollow to accommodate the guide wire (38). The shaft of this lumen allows the push and opening of the atrial segment of the capsule. An additional shaft layer travels the capsule and the endoprosthesis is crimped on it. This layer has a plurality of pins at the level of the stent ring (43) on which the stent is passively stabilized by mirroring elements at its exterior surface.

The ventricular segment of the capsule is connected to an additional shaft layer (44) that is found on the delivery system (not in the capsule). A part of this layer starting at the capsule and having sufficient length can effortlessly expand to accommodate a part of the endoprosthesis in case it needs to be removed after complete deployment. This is required because the ventricular segment of the capsule is smaller and cannot accommodate the entire length of the collapsing stent and wire mesh. The entire length of the endoprosthesis needs to be sheathed in order the atrial capsule part to come close, meet and attach its ventricular part and the entire capsule safely removed.

When the delivery is considered successful and the holding wires are removed, the empty atrial capsule segment is withdrawn to meet and attach to the also empty ventricular capsule segment and then the capsule is closed and removed in one piece (FIG. 3D).

The shaft of the delivery system that connects the capsule to the handle has the previously described layers plus a space (could be in the form of an additional lumen) to accommodate the retracting holding wires of the endoprosthesis (45).

The handle is where all the above-described components of the shaft culminate. It has a central lumen for the guide wire to exit (46) and all the necessary knobs/dials/wheels (47) to facilitate the independent motions of the two capsule segments, and the thin wires that are used to resheath and remove the valve if needed. It is envisaged that one knob/dial/wheel is required for the movement of the atrial capsule, one for the movement of the ventricular capsule and possibly one for the pulling of the holding wires.

The delivery catheter is advanced in the left ventricle by itself or through a guide sheath. The guide sheath and/or the delivery catheter can have flexing capabilities to assist the coaxial and central to the annulus positioning of the capsule before and during delivery.

Considering the endoprostheses of the embodiments 3, 4b and 5 the delivery catheter is similar, but the capsule does not split into two parts, and it opens from its atrial tip towards the ventricle (the endoprosthesis of the embodiment 1 can also be released such a way) (FIG. 4B, 4C, 4D). First, the wire mesh is released completely within the atrium. The entire device then is pulled downward till the wire mesh seats firmly at the floor of the atrium. Then the capsule is further withdrawn releasing gradually the wire frame that apposes to the annulus and the crown components of the stent part in embodiments 3 and 4b or the ventricular part of the wire mesh in the embodiment 5.

The wire frame of the endoprosthesis and the course of the anchoring structures allow for complete retrieval of the endoprosthesis even after complete release.

The unnecessary parts of the delivery catheter for delivering this endoprosthesis are omitted (such as the separate shaft layer for the stabilization pins of the endoprosthesis and the handle wheel for moving the atrial segment of the capsule). A plurality of holding wires for retrieval of the endoprosthesis is reversibly attached (as described before) at the tips of the anchoring or other structures of the stent crown. By pulling these, the endoprosthesis reenters into the delivery capsule.

Figure 11:
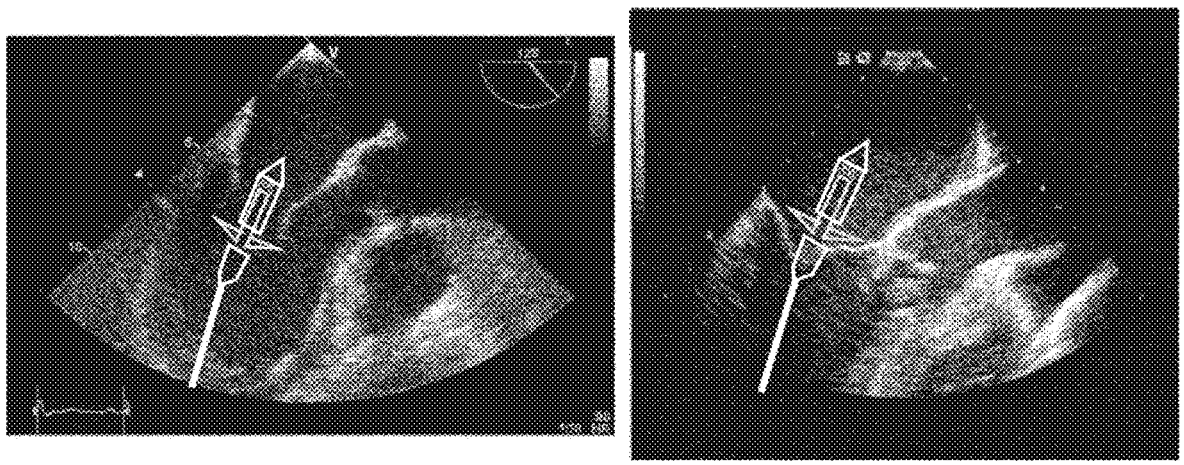
FIG. 11 shows the initial part of a transapical deployment of a prosthetic valve according to the present invention.
Figure 12:
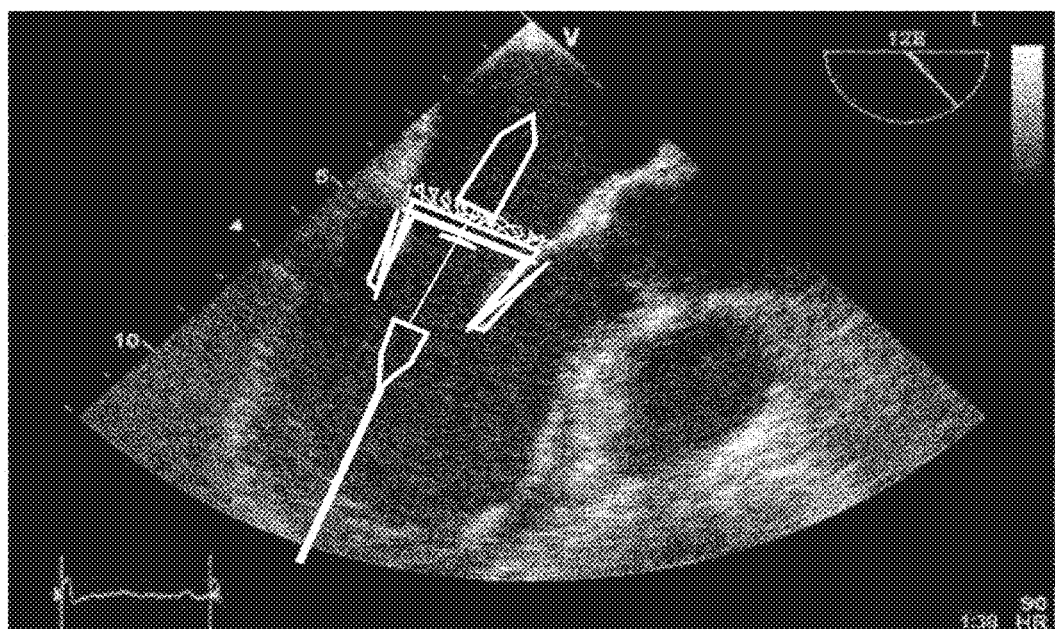
FIG. 12 shows a transapically deployed prosthetic valve according to the present invention.

FIGS. 11 and 12 illustrate an example of transapical delivery of one of the embodiments described.

2. Antegrade Access (Transeptal, or Direct Approach)

Figure 13:
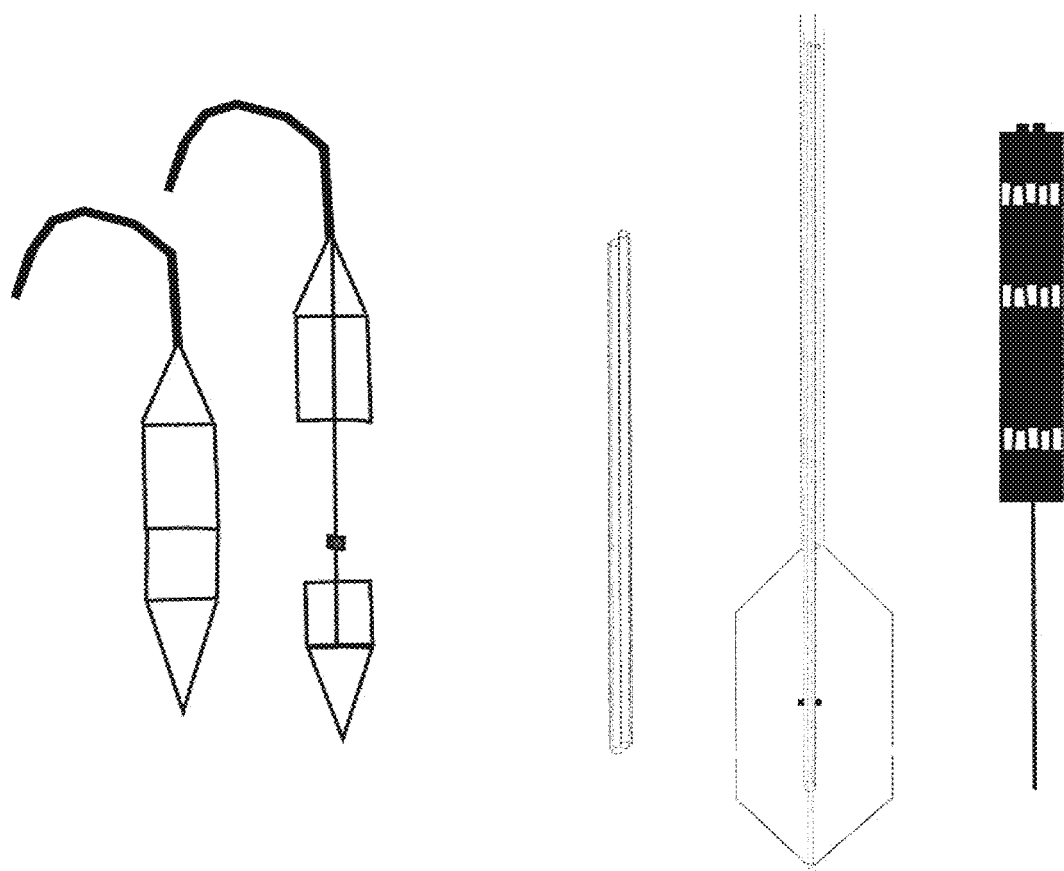
FIG. 13 shows a further embodiment of a catheter for the delivery of a prosthetic valve according to the present invention.

The delivery catheter for the endoprosthesis of all embodiments consists of the endoprosthesis capsule, the shaft and the handle (FIG. 13). They all share a central lumen that accommodates the guide wire over which the device is railed at the intended position of deployment.

The capsule contains the collapsed and crimped endoprosthesis. Its both ends are conical to allow smooth tracking forward and backward.

Figure 14:
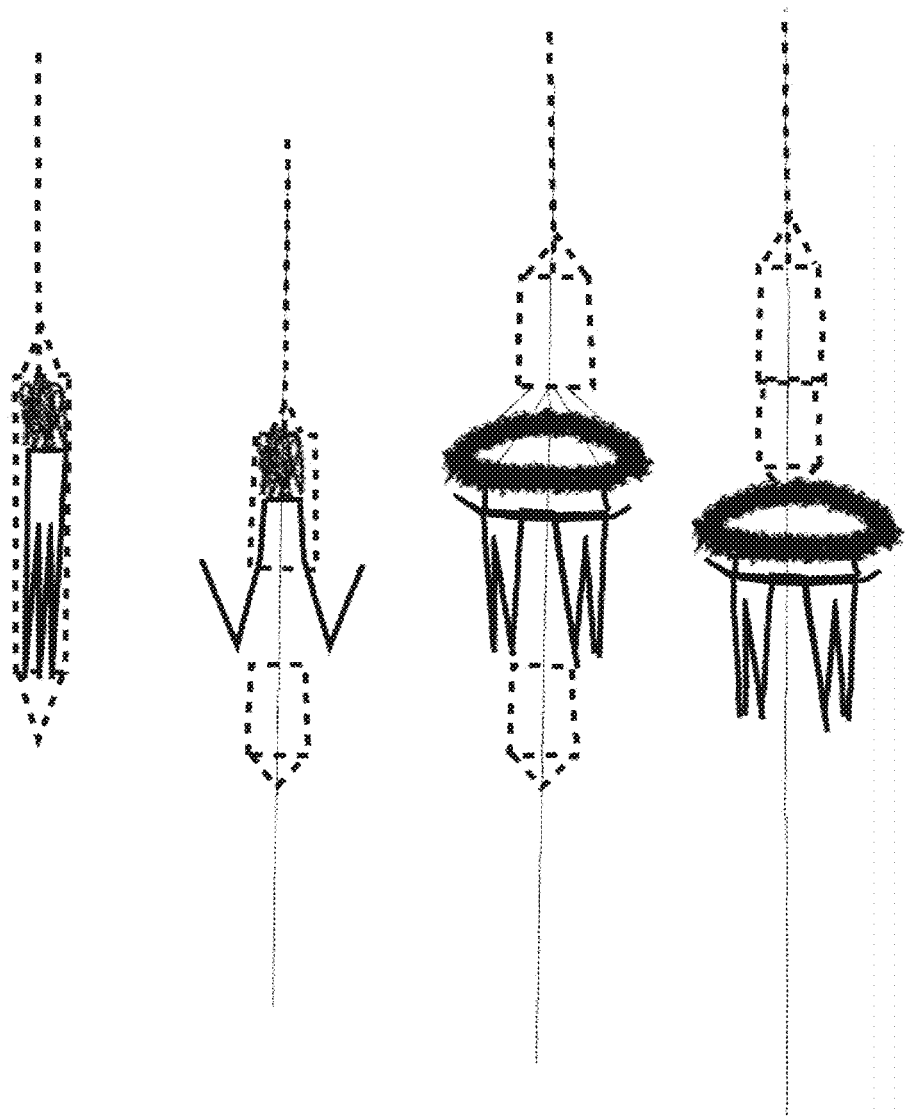
FIG. 14 shows one way of releasing a prosthetic valve according to the invention from its capsule.

For the endoprosthesis of the embodiments 1, 2 and 4a the capsule opens in two parts, the atrial part is longer and the ventricular part is shorter (FIG. 14). Each of these parts can move and open/close the respective part of the capsule independently. First the ventricular part is opened (advanced/pushed) and the part of the endoprosthesis crimped in this part expands, namely the external capturing elements of the native valve leaflets expand fully, while their internal counterparts start to flare. When the external capturing elements are positioned deep behind the native leaflets and in contact to the ventricular side of the annulus, the atrial part of the capsule is opened (withdrawn/pulled back) releasing gradually first the internal capturing elements of the stent crown, then the stent ring and finally the wired mesh. When the endoprosthesis is fully deployed and functional it is still connected to the delivery catheter with a plurality of thin wires (such as ultra thin nitinol wires) or screwing wires attached at the most atrial edges of the wire mesh. Therefore complete atraumatic removal of the endoprosthesis is still feasible. When thin wires are used, they are threaded trough suitable features of the wire mesh. If the endoprosthesis position and function is satisfactory, one end is pulled till the entire thread is removed from the endoprosthesis and releases it. If the endoprosthesis needs to be removed both ends of the nitinol wires are pulled, and it is gradually retracted into the atrial capsule. Another way of reversible connection of the thin wires to the mesh is with the Highwayman's knot that allows tightening the knot and tugging by pulling one end of the wire, while the knot unties easily by pulling the other end of the wire.

Finally, an alternative way of attachment is by use of screwing wires that are fixed in female parts in the mesh.

The part of the shaft traveling inside through the capsule has an inner lumen to accommodate the guide wire. The shaft of this lumen allows the push and opening of the ventricular segment of the capsule. An additional shaft layer travels the capsule and the endoprosthesis is crimped on it. This layer has a plurality of pins at the level of the stent ring on which the stent is passively stabilized by mirroring elements at its exterior surface.

The atrial segment of the capsule is connected to an additional shaft layer that is found on the delivery system (not in the capsule). This withdraws the atrial segment of the capsule, to completely release the endoprosthesis.

A part of this layer starting at the capsule and having sufficient length can effortlessly expand to accommodate a part of the endoprosthesis in case this needs to be removed after complete deployment. This is required because the entire length of the endoprosthesis needs to be sheathed into the atrial segment of the capsule. This additional space is required for the length of the stent that used to be accommodated into the ventricular capsule. The entire length of the endoprosthesis needs to be sheathed into the atrial capsule for the ventricular capsule segment to attach and close the capsule for safe removal.

If the deployment is not satisfactory, the wire mesh is first resheathed into the longer atrial capsule. The small part of the endoprosthesis that used to be accommodated into the ventricular capsule is also retracted into the atrial capsule, as described. When the delivery is considered successful and the holding wires are removed, the empty ventricular capsule segment is withdrawn to meet and attach to the also empty atrial capsule segment and they are then removed en block.

The shaft of the delivery system that connects the capsule to the handle has the previously described layers plus a space (could be in the form of an additional lumen) to accommodate the holding/retracting wires of the endoprosthesis.

The handle is where all the above-described components of the shaft culminate. It has a central lumen for the guiding wire to exit and all the necessary knobs/dials to facilitate the independent motions of the two capsule segments, and the wires that can be used to resheath and remove the valve if needed. It is envisaged that one knob/dial is required for the movement of the atrial capsule, one for the movement of the ventricular capsule and possibly one for the pulling of the holding wires.

The delivery catheter is advanced in the left atrium through a transeptal sheath or with direct access. The transeptal sheath and/or the delivery catheter can have flexing capabilities to assist the coaxial and central to the annulus positioning of the capsule before and during delivery.

Considering the endoprostheses of the embodiments 3, 4b and 5, the delivery catheter is similar, but the capsule does not split into two parts, and it opens from its atrial tip towards the ventricle (the endoprosthesis of the embodiment 1 can also be released such a way) (FIG. 4B, 4C, 4D). First, the wire mesh is released completely within the atrium by advancing the capsule towards the ventricle. The entire device then is pushed downward till the wire mesh seats firmly at the floor of the atrium. Then the capsule is further advanced releasing gradually the rest of the wire frame that apposes to the annulus and the crown components of the stent part in embodiments 3 and 4 or the ventricular part of the wire mesh in the embodiment 5.

The wire frame of the endoprosthesis and the course of the anchoring structures allow for complete retrieval of the endoprosthesis even after complete release.

A plurality of holding wires for retrieval of the endoprosthesis is reversibly attached (as described before) at the atrial edges of the wire mesh. By pulling these, the endoprosthesis reenters into the atrial segment of the delivery capsule.

Figure 15:
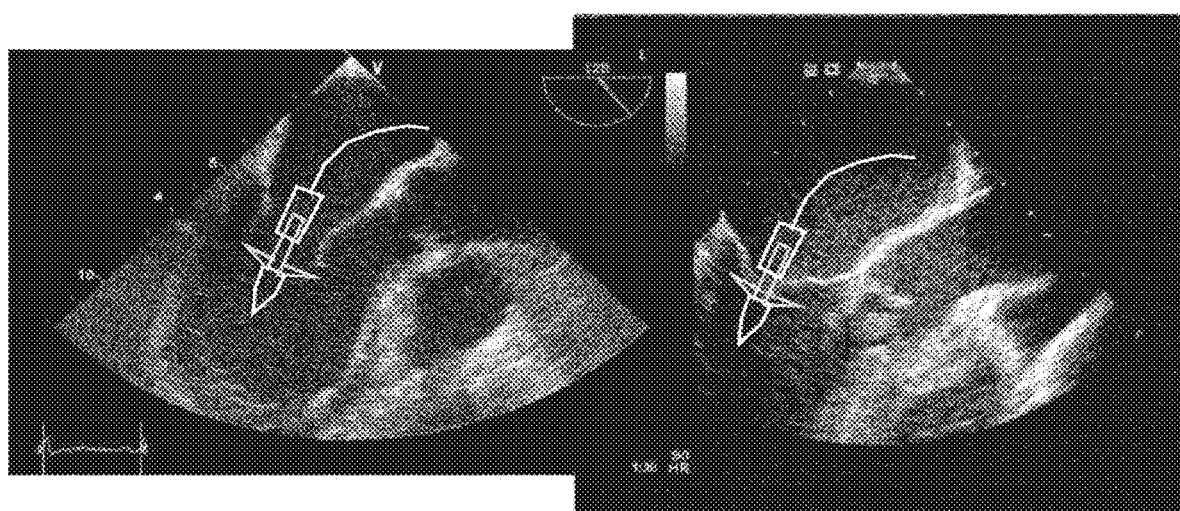
FIG. 15 shows the initial part of a transatrial/transeptal deployment of a prosthetic valve according to the present invention.
Figure 16:
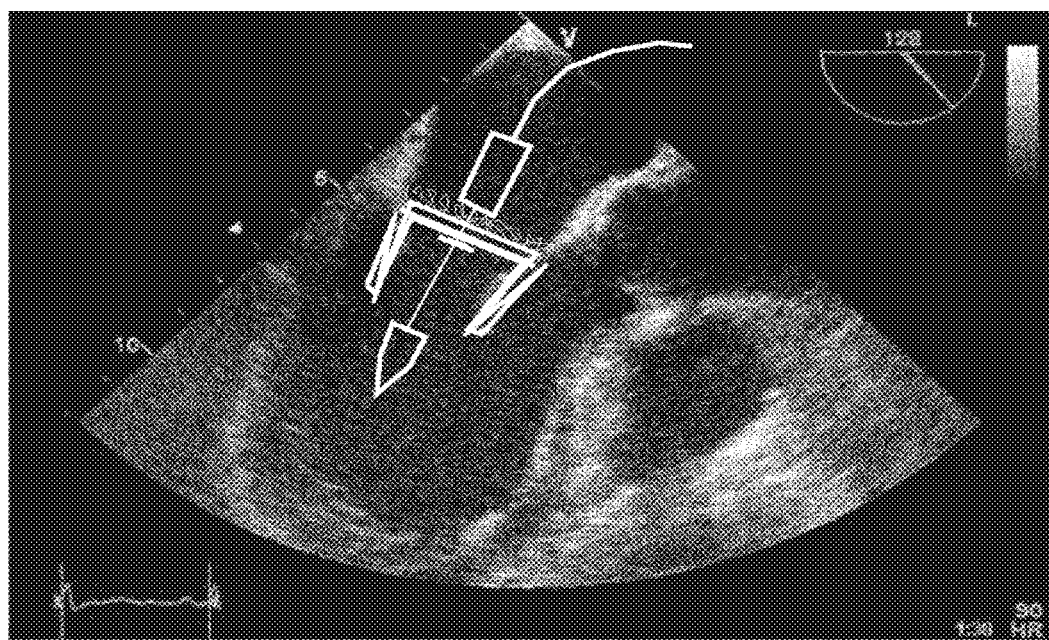
FIG. 16 shows a transatrially/transeptally deployed prosthetic valve according to the present invention.

FIGS. 15 and 16 illustrate an example of transapical delivery of one of the embodiments described.

In summary, the claimed inventions provide for all aspects of a successful transcatheter prosthetic mitral valve. They resolve the problems related to the uneven anatomy of the mitral valve by offering remedies at the level of the mitral valve leaflets (capture in a wide-open position and stabilization at the ventricular side), at the level of the annulus (optimal apposition, sealing and stabilization by the prosthetic valve frame) and at the level of the atrial floor (optimal apposition, sealing and stabilization by the prosthetic valve frame).

These are achieved with: 1. A refined combination of two components in the frame of the endoprosthesis, namely the wire stent contributing optimal radial strength for the formation of the frame lumen and the orifice of the prosthetic valve and the wire mesh contributing plasticity and optimal conformation. 2. An innovative method to capture and immobilize the native valve leaflets and navigationally guides the deployment of the prosthetic valve offering tactile feedback and at the same time the much-required stabilization at the ventricular level.

What is claimed is:

1. A method of implanting a prosthetic mitral valve in a native mitral valve, comprising:
   advancing a delivery catheter through an atrial septum in a human heart and toward a native mitral valve, the delivery catheter having a distal capsule containing a prosthetic mitral valve in a compressed state, the prosthetic mitral valve including:
   a self-expandable interior stent defining a lumen supporting a plurality of valve leaflets, the interior stent covered at least in part by a sealing skirt, the interior stent having a plurality of native leaflet capturing elements extending from a ventricular end; and
   a self-expandable exterior wire mesh surrounding the interior stent, the exterior wire mesh extending along substantially an entire length of the interior stent, the exterior wire mesh having a lower radial strength than the interior stent for conforming to a native mitral valve, the exterior wire mesh attached to an atrial end of the interior stent;
   expelling the prosthetic mitral valve from the distal capsule;
   allowing the prosthetic mitral valve to self-expand within the native mitral valve;

wherein, in an expanded state, the exterior wire mesh has an enlarged diameter positioned above a mitral annulus and a reduced diameter contacting the mitral annulus and wherein the capturing elements of the interior stent extend in a ventricular direction beyond the exterior wire mesh and then turn in an atrial direction such that native mitral leaflets are trapped between the capturing elements and an outer surface of the wire mesh.

2. The method according to claim 1, wherein the wire mesh reaches the ventricular end of the interior stent.

3. The method according to claim 1, wherein the wire mesh extends beyond the ventricular end of the interior stent.

4. The method according to claim 1, wherein the distal capsule is tapered along its proximal and distal ends for facilitating advancement and retraction.

5. The method according to claim 1, wherein the native leaflet capturing elements have different shapes.

6. The method according to claim 1, wherein the wire mesh comprises a fabric sealing material.

7. The method according to claim 1, wherein the delivery catheter is advanced over a guide wire to the native mitral valve.

8. The method according to claim 1, wherein the wire mesh includes barbs or spikes along the outer surface.

9. The method according to claim 1, wherein a handle is provided on the proximal end portion of the delivery catheter and wherein knobs on the handle are actuated for releasing the prosthetic mitral valve from the distal capsule.

10. A method of implanting a prosthetic valve in a native valve, comprising:
   advancing a flexible elongate delivery catheter into a human heart and toward a native valve, the delivery catheter having a distal capsule containing a prosthetic valve in a compressed state, the prosthetic valve including:
      a self-expandable interior stent defining a lumen supporting a plurality of leaflets, the interior stent covered at least in part by a fabric sealing skirt, the interior stent having a plurality of capturing elements extending from a ventricular end; and
      a self-expandable exterior wire mesh surrounding the interior stent, the exterior wire mesh extending along substantially an entire length of the interior stent, the exterior wire mesh having a lower radial strength than the interior stent for conforming to a shape of a native valve, wherein the exterior wire mesh is attached to an atrial end portion of the interior stent;
   expelling the prosthetic valve from the distal capsule;
   allowing the prosthetic valve to self-expand within the native valve;
   wherein, in an expanded state, the exterior wire mesh has an enlarged diameter positioned on an atrial side of a native annulus and a reduced diameter contacting the native annulus and wherein the capturing elements of the interior stent extend in a ventricular direction beyond the exterior wire mesh and then turn in an atrial direction such that leaflets of the native valve are positioned between the capturing elements and an outer surface of the wire mesh.

11. The method according to claim 10, wherein the wire mesh reaches the ventricular end of the interior stent.

12. The method according to claim 10, wherein the wire mesh extends beyond the ventricular end of the interior stent.

13. The method according to claim 10, wherein the distal capsule is tapered along its proximal and distal ends for facilitating advancement and retraction.

14. The method according to claim 10, wherein the native leaflet capturing elements have different shapes.

15. The method according to claim 10, wherein the interior stent and exterior wire mesh are both made of nitinol.

16. The method according to claim 10, wherein the delivery catheter is advanced over a guide wire to the native valve.

17. The method according to claim 10, wherein the wire mesh includes barbs or spikes along the outer surface for enhancing securement to the native valve.

18. The method according to claim 10, wherein a handle is provided on the proximal end portion of the delivery catheter and wherein knobs on the handle are actuated for releasing the prosthetic valve from the distal capsule.

\* \* \* \* \*